United States Patent
Roy et al.

(10) Patent No.: US 9,447,125 B2
(45) Date of Patent: Sep. 20, 2016

(54) REUSABLE HOMOGENEOUS COBALT PYRIDINE DIIMINE CATALYSTS FOR DEHYDROGENATIVE SILYLATION AND TANDEM DEHYDROGENATIVE-SILYLATION-HYDROGENATION

(71) Applicants: Aroop Kumar Roy, Mechanicville, NY (US); Crisita Carmen Hojilla Atienza, Houston, TX (US); Paul J. Chirik, Princeton, NJ (US); Kenrick M. Lewis, Flushing, NY (US); Keith J. Weller, Rensselaer, NY (US); Susan Nye, Feura Bush, NY (US); Johannes G. P. Delis, Bergen op Zoom (NL); Julie L. Boyer, Watervliet, NY (US); Tianning Diao, Plainsboro, NJ (US); Eric Pohl, Mount Kisco, NY (US)

(72) Inventors: Aroop Kumar Roy, Mechanicville, NY (US); Crisita Carmen Hojilla Atienza, Houston, TX (US); Paul J. Chirik, Princeton, NJ (US); Kenrick M. Lewis, Flushing, NY (US); Keith J. Weller, Rensselaer, NY (US); Susan Nye, Feura Bush, NY (US); Johannes G. P. Delis, Bergen op Zoom (NL); Julie L. Boyer, Watervliet, NY (US); Tianning Diao, Plainsboro, NJ (US); Eric Pohl, Mount Kisco, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 14/270,710

(22) Filed: May 6, 2014

(65) Prior Publication Data
US 2014/0243486 A1    Aug. 28, 2014

Related U.S. Application Data

(63) Continuation-in-part of application No. 13/966,568, filed on Aug. 14, 2013, now Pat. No. 8,927,674.

(60) Provisional application No. 61/819,761, filed on May 6, 2013, provisional application No. 61/819,753, filed on May 6, 2013, provisional application No. 61/683,882, filed on Aug. 16, 2012.

(51) Int. Cl.
| | |
|---|---|
| *C08G 77/06* | (2006.01) |
| *C07F 7/18* | (2006.01) |
| *C07F 7/08* | (2006.01) |
| *C08G 77/38* | (2006.01) |
| *B01J 31/18* | (2006.01) |
| *C07F 15/06* | (2006.01) |
| *C08L 83/04* | (2006.01) |
| *C08L 83/14* | (2006.01) |
| *C08G 77/04* | (2006.01) |
| *C08G 77/12* | (2006.01) |
| *C08G 77/20* | (2006.01) |

(52) U.S. Cl.
CPC .......... *C07F 7/1876* (2013.01); *B01J 31/1815* (2013.01); *C07F 7/0829* (2013.01); *C07F 7/0849* (2013.01); *C07F 7/0852* (2013.01); *C07F 7/0854* (2013.01); *C07F 7/0879* (2013.01); *C07F 7/184* (2013.01); *C07F 7/1836* (2013.01); *C07F 15/065* (2013.01); *C08G 77/38* (2013.01); *C08L 83/04* (2013.01); *C08L 83/14* (2013.01); *B01J 2231/323* (2013.01); *B01J 2531/0241* (2013.01); *B01J 2531/0244* (2013.01); *B01J 2531/845* (2013.01); *C08G 77/12* (2013.01); *C08G 77/20* (2013.01)

(58) Field of Classification Search
CPC .... C08F 10/10; C08F 210/16; B01J 31/1805
USPC .......... 502/150, 162, 167, 405, 406; 528/31, 528/32, 402, 405, 406
See application file for complete search history.

(56) References Cited

U.S. PATENT DOCUMENTS

| | | | |
|---|---|---|---|
| 3,159,601 | A | 12/1964 | Ashby et al. |
| 3,220,972 | A | 11/1965 | Lamoreaux |
| 3,296,291 | A | 1/1967 | Chalk et al. |
| 3,775,452 | A | 11/1973 | Karstedt |
| 3,928,629 | A | 12/1975 | Chandra et al. |
| 4,550,152 | A | 10/1985 | Faltynek |
| 4,572,971 | A | 2/1986 | Necoechea |
| 4,578,497 | A | 3/1986 | Onopchenko et al. |
| 4,729,821 | A | 3/1988 | Timmons et al. |
| 4,788,312 | A | 11/1988 | Paciorek et al. |
| 5,026,893 | A | 6/1991 | Paciorek |
| 5,166,298 | A | 11/1992 | Friedmann et al. |
| 5,331,075 | A | 7/1994 | Sumpter et al. |
| 5,432,140 | A | 7/1995 | Sumpter et al. |
| 5,866,663 | A | 2/1999 | Brookhart et al. |
| 5,955,555 | A | 9/1999 | Bennett |
| 6,103,946 | A | 8/2000 | Brookhart et al. |
| 6,214,761 | B1 | 4/2001 | Bennett |
| 6,265,497 | B1 | 7/2001 | Herzig |
| 6,278,011 | B1 | 8/2001 | Chen et al. |

(Continued)

FOREIGN PATENT DOCUMENTS

| | | |
|---|---|---|
| CN | 1727349 | 2/2006 |
| EP | 0786463 | 7/1997 |

(Continued)

OTHER PUBLICATIONS

Tondreau, et al., "Iron Catalysts for Selective Anti-Markovnikov Alkene Hydrosilylation Using Tertiary Silanes," Science, vol. 335, No. 6068, Feb. 2, 2012 (Feb. 2, 2012). pp. 567-570.

(Continued)

*Primary Examiner* — Terressa Boykin
(74) *Attorney, Agent, or Firm* — Joseph E. Waters; McDonald Hopkins LLC

(57) ABSTRACT

Disclosed herein are cobalt complexes containing terdentate pyridine di-imine ligands and their use as efficient, reusable, and selective dehydrogenative silylation, crosslinking, and tandem dehydrogenative silylation-hydrogenation catalysts.

40 Claims, No Drawings

(56) References Cited

U.S. PATENT DOCUMENTS

| | | | |
|---|---|---|---|
| 6,281,303 B1 | 8/2001 | Lavoie et al. | |
| 6,297,338 B1 | 10/2001 | Cotts et al. | |
| 6,417,305 B2 | 7/2002 | Bennett | |
| 6,423,848 B2 | 7/2002 | Bennett | |
| 6,432,862 B1 | 8/2002 | Bennett | |
| 6,451,939 B1 | 9/2002 | Britovsek | |
| 6,455,660 B1 | 9/2002 | Clutton et al. | |
| 6,458,739 B1 | 10/2002 | Kimberley et al. | |
| 6,458,905 B1 | 10/2002 | Schmidt et al. | |
| 6,461,994 B1 | 10/2002 | Gibson et al. | |
| 6,472,341 B1 | 10/2002 | Kimberley et al. | |
| 6,620,895 B1 | 9/2003 | Cotts et al. | |
| 6,657,026 B1 | 12/2003 | Kimberley et al. | |
| 7,053,020 B2 | 5/2006 | De Boer et al. | |
| 7,148,304 B2 | 12/2006 | Kimberly et al. | |
| 7,161,005 B2 | 1/2007 | Schlingloff et al. | |
| 7,247,687 B2 | 7/2007 | Cherkasov et al. | |
| 7,268,096 B2 | 9/2007 | Small et al. | |
| 7,429,672 B2 | 9/2008 | Lewis et al. | |
| 7,442,819 B2 | 10/2008 | Ionkin et al. | |
| 7,456,285 B2 | 11/2008 | Schlingloff et al. | |
| 7,696,269 B2 | 4/2010 | Cruse et al. | |
| 8,236,762 B2 | 8/2012 | Dong et al. | |
| 8,236,915 B2 | 8/2012 | Delis et al. | |
| 8,415,443 B2* | 4/2013 | Delis et al. | 528/14 |
| 2002/0058584 A1 | 5/2002 | Bennett | |
| 2006/0263675 A1 | 11/2006 | Adzic et al. | |
| 2007/0264189 A1 | 11/2007 | Adzic et al. | |
| 2008/0262225 A1 | 10/2008 | Schlingloff et al. | |
| 2008/0293878 A1 | 11/2008 | Funk et al. | |
| 2009/0068282 A1 | 3/2009 | Schlingloff et al. | |
| 2009/0296195 A1 | 12/2009 | Fontana et al. | |
| 2011/0009565 A1* | 1/2011 | Delis | B01J 31/1815 525/102 |
| 2011/0009573 A1* | 1/2011 | Delis | C07F 15/02 525/453 |
| 2012/0130021 A1* | 5/2012 | Tondreau | C07F 7/0829 525/342 |
| 2012/0130105 A1 | 5/2012 | Lewis et al. | |
| 2012/0130106 A1 | 5/2012 | Chirik et al. | |
| 2013/0158281 A1 | 6/2013 | Weller et al. | |
| 2014/0051822 A1* | 2/2014 | Atienza | B01J 31/1815 528/31 |
| 2014/0243486 A1 | 8/2014 | Roy et al. | |
| 2014/0330036 A1* | 11/2014 | Lewis | C07F 7/0829 556/481 |
| 2015/0080536 A1* | 3/2015 | Diao | B01J 31/1815 525/479 |

FOREIGN PATENT DOCUMENTS

| | | |
|---|---|---|
| GB | 2013207 | 8/1979 |
| TW | 200902541 | 1/2009 |
| WO | 9210544 | 6/1992 |
| WO | 02088289 | 11/2002 |
| WO | 03042131 | 5/2003 |
| WO | 2008085453 | 7/2008 |
| WO | 2011006044 | 1/2011 |
| WO | 2012071359 | 5/2012 |
| WO | 2013/043783 A2 | 3/2013 |
| WO | 2013/043846 A1 | 3/2013 |
| WO | 2013043846 | 3/2013 |

OTHER PUBLICATIONS

Abu-Surrah et al., "New bis(imino)pyridine-iron(II)- and cobalt(II)-based catalysts: synthesis, characterization and activity towards polymerization of ethylene" Journal of Organometallic Chemistry 648 (2002) 55-61.

Albon et al., "Metal Carbonyl Complexes Involving 2,6Bix[l-(phenylimino)ethyl]pyridine; Bidentate Corrdination of a Potentially Tridentate Ligand" Inorganica Chimica Acta, 159 (1989) 19-22.

Alyea et al., "Terdentate NNN Donor Ligands Derived from 2,6-Diacetylpyridine" Syn. React. Inorg. Metal-Org. Chem., 4(6), 535-544 (1974).

Bouwkamp, "Iron-Catalyzed [2π+2π] Cycloaddition of a,ω-Dienes the Importance of Redox Active Supporting Ligands" Journal of the American Chemical Society, 2006, V128 N41, P13340-13341.

Britovsek et al., "Novel Olefin Polymerization Catalysts Based on Iron and Cobalt," Chem. Commun., 1998, 849-850.

Cetinkaya et al., "Ruthenium(ii) complexes with 2,6-pyridyl-diimine ligands: synthesis, characterization and catalytic activity in epoxidation reactions" Journal of Molecular Catalysis A: Chemical 142 (1999) 101-112.

Corey et al., "Reactions of Hydrosilanes with Transition-Metal Complexes: Formation of Stable Transition-Metal Silyl Compounds," Journal of Chemical Reviews, vol. 99, pp. 175-292 (1999).

Haarman et al., "Reactions of [RhCl(diene)]2 with Bi- and Terdentate Nitrogen Ligands. X-ray Structures of Five-Coordinate Complexes," Am. Chem. Soc., Organometallics 1997, 16, 54-67.

International Search Report and Written Opinion of the International Searching Authority for PCT/US2014/036935 mailed Jul. 10, 2014.

Kickelbick et al., New J. Chem., 2002, 26, 462-468.

Kooistra et al., Inorganica Chimica Acta 357 (2004) 2945-2952.

Lapointe, et al., "Mechanistic Studies of Palladium(II)-Catalyzed Hydrosiliation and Dehydrogenative Silation Reactions," J. Amer. Chem. Soc. 119 (1997), pp. 906-917.

Lewis et al., "Hydrosilylation Catalyzed by Metal Colloids: A Relative Activity Study," Organometallics, 9 (1990), 621-625.

Lions et al., J. Chem. Soc. (A) 1957, vol. 79, 2733-2738.

Lu et al., "The Molecular Structure of a Complex of a 2,6-Diimino-Pyridine as a Bidentate Liandd with Molybdenum Carbonyl" Inorganica Chimica Acta, 134 (1987) 229-232.

Pangborn, et al., "Safe and Convenient Procedure for Solvent Purification," Oraganometallics, 15:1518 (1996).

Randolph, Claudia L. et al., "Photochemical Reactions of (η5-Pentamethylcyclopentadienyl)dicarbonyliron-Alkyl and Silyl Complexes: Reversible Ethylene Insertion into an Iron-Silicon Bond and Implications for the Mechanism of Transition-Metal-Catalyzed Hydrosilation of Alkenes," Journal of the American Chemical Society, vol. 108, pp. 3366-3374 (1986).

Russell et al., "Synthesis of Aryl-Substituted Bis(imino)pyridine Iron Dinitrogen Complexes," Inorg. Chem. 2010, 49, 2782-2792.

Sacconi et al., J. Chem. Soc. (A), 1968, 1510-1515.

Speier, J. L.; Webster, J. A.; Barnes, G. H. J. Am. Chem. Soc. 1957, 79, 974.

Ittel et al., DuPont's Versipol®Late Metal Polymerization Catalysts, http://www.nacatsoc.org/18nam/Orals/044-Ittel-DuPont's%20Versipol%C2%AE%20Late%20Metal%20Polymerization.pdf.

Toma et al., J. Braz. Chem. Soc., vol. 7, No. 6, 391-394, 1996.

Tondereau, et al., "Enantiopure Pyridine Bis(oxazoline) "Pybox" and Bis(oxazoline) "Box" iron Dialkyl Complexes: Comparison to Bis(imino)pyridine Compounds and Application to Catalytic Hydrosilylation of Ketones," Organometallics, Jun. 9, 2009, 28(13), 3928-3940.

Suzuki, et al., "Random and block copolymerizations of norbornene with conjugated 1,3-dienes catalyzed by novel No compounds involving N- or O-donated ligands" Reactive & Functional Polymers 59 (2004) 253-266, May 6, 2004.

Kuo, et al., "Electrochemical studies of nickel bis(2,2':6',2"-terpyridine) with alkyl/aryl/allyl bromides and activated olefins in nonaqueous solvents" Jiemian Kexue Huishi, vol. 15, Issue 1, pp. 23-42, Journal, 1992, Coden: CMKCEW, ISSN: 1026-325X.

Chen et al., "General Synthesis of Di-u-oxo Dimanganese Complexes as Functional Models for the Oxygen Evolving Complex of Photosystem II" Inorg. Chem. 2005, 44, 7661-7670.

Yeung, et al., "Cobalt and iron complexes of chiral C1- and C2-terpyridines: Synthesis, characterization and use in catalytic asymmetric cyclopropanation of styrenes." Inorganica Chimica Acta 362 (2009) 3267-3273.

Archer et al., "Arene Coordination in Bis(imino)pyridine Iron Complexes: Identification of Catalyst Deactivation Pathways in Iron-Catalyzed Hydrogenation and Hydrosilation," Organometallics, vol. 25, pp. 4269-4278 (2006).

(56) References Cited

OTHER PUBLICATIONS

Bowman et al., "Reduced N-Alkyl Substituted Bis(imino)pyridine Cobalt Complexes: Molecular and Electronic Structures for Compounds Varying by Three Oxidation States," Inorg. Chem. 2010, 49, 6110-6123, Germany.

Zhu et al., A Measure for *-Donor and *-Acceptor Properties of Diiminepyridine-Type Ligands, Organometallics 2008, 27, 2699-2705.

Atienza "Improving the Conditions and Expanding the Scope of Bis(imino)pyridine Iron-Catalyzed Olefin Hydrosilyation." (Dissertation) Chapter 7.

International Preliminary Report on Patentability for PCT/US2010/041487 dated Jan. 19, 2012.

Bart et al., "Electronic Structure of Bis(imino)pyridine Iron Dichloride, Monochloride, and Neutral Ligand Complexes: A Combined Structural, Spectroscopic, and Computational Study," J. Am. Chem. Soc. 2006, 128, 13901-13912.

Bart et al., "Preparation and Molecular and Electronic Structures of Iron(0) Dinitrogen and Silane Complexes and Their Application to Catalytic Hydrogenation and Hydrosilation," Journal of the American Chemical Society, vol. 126, pp. 13794-13807 (2004).

Connelly et al., "Chemical Redox Agents for Organometallic Chemistry," Chem. Rev. 1996, 96, 877-910.

Atienza et al. "Synthesis, Electronic Structure, and Ethylene Polymerization Activity of Bis(imino)pyridine Cobalt Alkyl Cations," Agnewandte Chem. Int. Ed. 2011, 50, 8143-8147.

Glatz et al., "Terpyridine-Based Silica Supports Prepared by Ring-Opening Metathesis Polymerization for the Selective Extraction of Noble Metals," Journal of Chromatography A, vol. 1015, pp. 65-71 (2003).

Nagashima et al., "Dehydrogenative Silylation of Ketones with a Bifunctional Organosilane by Rhodium- Pybox Catalysts," Chem. Soc. of Jpn., Chemistry Letters, 1993, 347-350, Toyohashi, Aichi 441.

Hosokawa et al., A Chiral Iron Complex Containing a Bis(oxazolinyl)phenyl Ligand: Preparation and Asymmetric Hydrosilylation of Ketones. Organometallics, 29, 5773-5775 (2010).

Kaul et al., Immobilization of Bis(imino)pyridyliron (II) complexes on Silica, Organometallics, 2002, 21(1), 74-83.

Kim et al., "2,2':6',2"-Terpyridine and Bis(2,2':6',2"-terpyridine)Ruthenium(II) Complex on the Dendritic Periphery," Journal of Organometallic Chemistry, vol. 673, pp. 77-83 (2003).

Kroll et al., "Access to Heterogeneous Atom-Transfer Radical Polymerization (ATRP) Catalysts Based on Dipyridylamine and Terpyridine via Ring-Opening Metathesis Polymerization (ROMP)," Macromolecular Chemistry and Physics, vol. 202, pp. 645-653 (2001).

Field et al., One-Pot Tandem Hydroamination/Hydrosilation Catalyzed by Cationic Iridium(I) Complexes, Organometallics, vol. 22, pp. 4393-4395, Sep. 25, 2003.

Dekamin et al., "Organocatalytic, rapid and facile cyclotrimerization of isocyanates using tetrabutylammonium phthalimide-N-oxyl and tetraethylammonium 2-(carbamoyl) benzoate under solvent-free conditions," Catalysis Communications 12 (2010) 226-230.

Nesmeyanov et al., "Addition, Substitution, and Telomerization Reactions of Olefins in the Presence of Metal Carbonyls or Colloidal Iron," Tetrahedron, vol. 17, pp. 61-68 (1962).

Pal, et al., Preparation and hydrosilylation activity of a molybdenum carbonyl complex that features a pentadentate bis (amino)pyridine lignad. Inorg Chem. Sep. 2, 2014; 53(17):9357-65. doi: 10.1021/ic501465v. Epub Aug. 20, 2014.

Jairam et al., "Ester Hydrolysis with 2,6-di(pyrazol-3-yl)pyridines and their Co 11 Complexes in Homogeneous and Micellar Media," Journal of Inorganic Biochemistry 84, 2001, 113-118, Toronto, Ontario, Canada.

Buschbeck et al., Triethylene Glycol Ether End-grafted Carbosilane Dendrimers: Synthesis and Complexation Behavior, Inorganic Chemistry Communications, vol. 7, pp. 1213-1216, Oct. 13, 2004.

Seckin, Preparation and Catalytic Properties of a Ru(II) Coordinated Polyimide Supported by a Ligand Containing Terpyridine Units, Journal of Inorganic and Organometallic Polymers and Materials, Apr. 9, 2009, 19(2), 143-151.

Sieh et al., Metal-Ligand Electron Transfer in 4d and 5d Group 9 Transition Metal Complexes with Pyridine, Diimine Ligands. Eur. J. Inorg. Chem., 2012:444-462. doi 10.1002/ejic.201101072.

Speier et al., "The Addition of Silicon Hydrides to Olefinic Double Bonds. Part II. The Use of Group VIII Metal Catalysts," Journal of the American Chemical Society, vol. 79, pp. 974-979 (1956).

Thammavongsy et al., Ligand-Based Reduction of CO2 and Release of CO and Iron(II). Inorg. Chem., 2012, 51 (17), pp. 9168-9170. DOI: 10:1021/ic3015404. Publication Date (Web): Aug. 20, 2012.

Timpa, "Non-Innocent Pyridine Based Pincer Ligands and Their Role Catalysis".

International Preliminary Report on Patentability for PCT/US2011/061746 dated Jun. 6, 2013.

Tondreau, et al "Synthesis and electronic structure of cationic, neutral, and anionic bis (imino)pyridine iron alkyl complexes: evaluation of redox activity in single-component ethylene polymerization catalysts." J Am Chem Soc. Oct. 27, 2010; 132(42): 15046-59. doi: 10.1021/ja106575b.

Gibson et al., "The nature of the active species in bis(imino)pyridyl cobalt ethylene polymerisation catalysts," Chem. Commun., 2001, 2252-2253.

Wile, et al. "Reduction chemistry of aryl- and alkyl-substituted bis(imino)pyridine iron dihalide compounds: molecular and electronic structures of [(PDI)2Fe] derivatives." Inorg Chem May 4, 2009; 48(9):4190-200.

International Preliminary Report on Patentability for PCT/US2012/069469 dated Mar. 12, 2014.

International Preliminary Report on Patentability for PCT/US2011/061752 dated May 28, 2013.

Anselment et al, "Activation of Late Transition Metal Catalysts for Olefin Polymerizations and Olefin/CO Copolymeriations," Dalton Transactions, vol. 34, pp. 4525-4672.

Atienza, et al., "Olefin hydrosilylation and dehydrogenative silylation with bis(imino) pyridine iron and cobalt catalysts," Abstracts of Papers, 244th ACS National Meeting & Exposition, Philadelphia, PA, Aug. 19-23, 2012.

Shaikh et al., "Iron-Catalyzed Enantioselevtive Hydrosilylation of Keytones," Angew. Chem. Int. Ed., 2008, 47, 2497-2501.

De Bo et al., "Hydrosilylation of Alkynes Mediated by N-heterocyclic Carben Platinum(0) Complexes," Organometallics, 2006, 25, 1881-1890.

Boudjouk et al., "Exclusive β-hydrosilylation of acrylates catalysed by copper-tetramethylethylenediamine," Journal of Organometallic Chemistry, Jan. 1, 1993, pp. 41-43.

Brookhart et al., "Mechanism of a cobalt(III)-catalyzed olefin hydrosilation reaction: direct evidence for a silyl migration pathway," J. Am. Chem. Soc. 1993, 115, 2151.

Castro, Pascel M. et al., "Iron-Based Catalysts Bearing Bis(imido)-Pyridine Ligands for the Polymerization of tert-Butyl Acrylate," Journal of Polymer Science: Part A: Polymer Chemistry, vol. 41, pp. 1380-1389 (2003).

Cornish, et al., "Homogeneous catalysis: VI. Hydrosilylation using tri(pentanedionato)rhodium(III) or tetrakis(µ-acetato) Dirhodium(II) as Catalysts," Journal of Organometallic Chemistry, Elsevier-Sequoia S.A. Lausanne, CH, vol. 172, No. 2, Jun. 12, 1979 (Jun. 12, 1979), pp. 153-163.

Chuit et al. "Reactivity of penta- and hexacoordinate silicon compounds and their role as reaction intermediates," Chem. Rev. 1993, 93, 1371-1448.

De Rycke et al., "Toward reactant encapsulation for substrate-selectivity," Tetrahedron Lett. 2012, 53, 462.

Doucette, "Homogeneous Iron Catalysts With Redox-Active Ligands: Synthesis and Electronic Structure," Dissertation Cornell University, Aug. 2006.

Doyle et al., "Addition/Elimination in the Rhodium(II) Perfluorobutyrate Catalyzed Hydrosilylationo of 1-Alkenes. Rhodium Hydride Promoted Isomerization and Hydrogenation," Organometallics, 1992, 11, 549-555, San Antonio, Texas.

(56) References Cited

OTHER PUBLICATIONS

Falck, J. R. et al. "Iridium-Catalyzed (Z)-Trialkylsilylation of Terminal Olefins," J. Org. Chem. 2010, 75, 1701.
Figgins et al., "Complexes of Iron(II), Cobalt(II) and Nickel(II) with Biacetyl-bis-methlylimine, 20Pyridinal-methylimine and 2,6-Pyridindial-bis-methylimine" J. Am. Chem. Soc. 1960, vol. 82, 820-824.
Gandon, et al., "Silicon-Hydrogen Bond Activation and Hydrosilylation of Alkenes Mediated by CpCo Complexes: A Theoretical Study," J. Am. Chem. Soc. 2009, 131, 3007.
Hori et al, "Ruthenium Complex-Catalyzed Silylation of Olefins. Selective Sysnthesis of Allysilanes," Bull. Chem. Soc. Jpn., 1988, 61, 3011-3013, Kyoto, Japan.
Humphries et al., "Investigations into the Mechanism of Activation and Initiation of Ethylene Polymerization by Bis (imino)pyridine Cobalt Catalysts: Synthesis, Structures, and Deuterium Labeling Studies," Organometallics 2005, 24, 2039-2050, London, United Kingdom.
Itoh et al, "Disproportionation reactions of organohydrosilanes in the presence of base catalysts" J. Organomet. Chem., 2001, 629, 1-6.
Ivchenko et al., "A convenient approach for the synthesis of 2,6-diformyl- and 2,6-diacetylpyridines," Tetrahedron Lett. 2013, 54, 217.
Fruchtel et al; "Organic Chemistry on Solid Supports," Angewandte Chemie International Edition in English, 1996, vol. 35, Issue 1, pates 17-42.
Junge et al., "Iron-Catalyzed Reducation of Carboxylic Esters to Alcohols," European Journal of Organic Chemistry, vol. 2013, No. 11, Mar. 1, 2013, pp. 2016-2065.
Kakiuchi et al., "Completely Selective Synthesis of (E)-B-(triethylsilyl)styrenes by Fe3(CO)12-catalyzed Reaction of Styrenes With Triethylsilane," Journal of Organometallic Chemistry 1993, 456, 45-47, Osaka, Japan.
Kakiuchi et al., "Dehydrogenative Silylation of 1,5-Dienes with Hydrosilanes Catalyzed by RhCI (PPh3)3," Am. Chem. Soc., Organometallics, 1993, 12, 4748-4750, Kagawa, Japan.
Kaverin et al., "Reaction of Polar Olefins with Methyldichlorosilane on nickel-containing Catalytic Systems," Chemical Abstracts Service.
Knijnenburg et al., "Olefin hydrogenation using diimine pyridine complexes of Co and Rh," Journal of Molecular catalysis, 232 (2005), No. 1-2, pp. 151-159.
Lu et al, "Iridium-Catalyzed (Z)-Trialkylsilylation ofTerminal Olefins," J. Org. Chem, 2010, 75, 1701-1705, Dallas, Texas.
Marciniec et al., "Competitve silylation of olefins with vinylsilanes and hydrosilanes photocatalyzed by iron carbonyl complexes," Inorg. Chem. Commun. 2000, 3, 371.
Marciniec, Bogdan, "Catalysis by Transition Metal Complexes of Alkene Silylation—Recent Progress and Mechanistic Implications," Coordination Chemistry Reviews, 249 (2009) 2374-2390.
Marciniec et al. "Encyclopedia of Catalysis" pp. 6,7, and 20, Mar. 5, 2010.
Martinez, Remi et al., "C-C Bond Formation via C-H Bond Activation Using an in Situ-Generated Ruthenium Catalyst," Journal of the American Chemical Society, vol. 131, pp. 7887-7895 (2009).
McAtee et al., "Preparation of Allyl and Vinyl Silanes by the Palladium-Catalyzed Silylation ofTerminal Olefins: A Silyl-Heck Reaction," Angewandte Chemie, Int. Ed. 2012, 51, 3663-3667.
McAtee et al., "Rational Design of a Second Generation Catalyst for Preparation of Allylsilanes Using the Silyl-Heck Reaction," J. Am. Chem. Soc. 2014, 136 (28), 10166-10172.
Bareille et al., "First Titanium-Catalyzed anti-1,4-Hydrosilylation of Dienes," Organometallics, 2005, 24(24), 5802-5806.
Niaumov et al, "Selective Dehydrogentative Silylation-Hydrogenation Reaction of Divinyldisiloxane with Hydrosilane catalyzed by an Iron Complex," Journal of the American Chemical Society, 2012, vol. 134, Issue 2, 804-807, Osaka, Japan.

Nishiyama et al., "An Iron-Catalysed Hydrosilylation of Ketones," Chem. Commun., Royal Society of Chemistry, 2007, 160-762.
Furuta et al., "Highly efficient catalytic system for hydrosilylation of ketones with iron(II) acetate—thiophenecarboxylate," Tetrahedron Letters, 2008, vol. 49, Issue 1, pp. 110-113.
Ojima et al., "Regioselective hydrosilylation of 1,3-dienes catalyzed by phosphine complexes of palladium and rhodium," J. Organomet. Chem. 1978, 157, 359-372.
Oro, L. A., et al. "Hydrosilylation of Alkenese by Iridium Complexes," J. Mol. Catalysis, 1986, 37, 151-156.
Pettigrew, "Synthetic Lubricants and High Performance Fluids, Ch. 12 Silahydrcarbons" (second edition), L. R. Rudnick and L R. Shubkin (Editors), Marcel Dekker, NY 1999, pp. 287-296.
Poyatos, Macarena et al., "Coordination Chemistry of a Modular N,C-Chelating Oxazole-Carbene Ligand and Its Applications in Hydrosilylation Catalysis," Organometallics, vol. 25, pp. 2634-2641 (2006).
Reiff, W. M. et al., "Mono(2,2',2"-terpyridine) Complexes of Iron(II)," Journal of Inorganic Chemistry, vol. 8, No. 9, pp. 2019-2021 (1969).
Parker et al. "1,2-Selective Hydrosilylation of Conjugated Dienes," J. Am. Chem. Soc., 2014, 136 (13), pp. 4857-4860.
Benkeser et al., "Chloroplatinic acid catalyzed additions of silanes to isoprene," J. Organomet. Chem. 1978, 156, 235-244.
Schmidt, Roland et al., "Heterogenized Iron(II) Complexes as Highly Active Ethene Polymerization Catalysts," Journal of Molecular Catalysis A: Chemical, vol. 179, pp. 155-173 (2002).
Seki et al., "Single-Operation Synthesis of Vinyl silanes from Alkenes and Hydrosilanes with the Aid of Ru (CO)12," Am. Chem. Soc., J. Org. Chem. 1986, 51, 3890-3895, Osaka, Japan.
Shaikh et al., "A Convenient and General Iron-Catalyzed Hydrosilylation of Aldehydes," Organic Letters, vol. 9, No. 26, Dec. 1, 2007, pp. 5429-5432.
Small, B. L., et al. "Highly Active Iron and Cobalt Catalysts for the Polymerization of Ethylene," J. Am. Chem. Soc. 1998, 120(16), 4049-4050.
Greenhalgh et al.,"Iron-Catalysed Chemo-, Regio-, and Stereoselective Hydrosilylation of Alkenes and Alkynes using a Bench-Stable Iron(II) Pre-Catalyst," Adv. Synth. Cata. 2014, 356(2-3), 584-590.
Woo et al., "Redistribution of Bos- and Tris(silyl)methanes Catalyzed by Red-Al," Bull. Korean. Chem. Soc. 1996, 17, 123-125.
Wu et al., "A Strategy for the Synthesis of Well-Defined Iron Catalysts and Application to Regioselective Diene Hydrosilylation," Journal of the American Chemical Society, vol. 132, No. 38. Sep. 29, 2010 (Sep. 29, 2010), pp. 13214-13216.
Yi, Chae S. et al., "Regioselective Intermolecular Coupling Reaction of Arylketones and Alkenes Involving C-H Bond Activation Catalyzed by an in Situ Formed Cationic Ruthenium Hydride Complex," Organometallics, vol. 28, pp. 4266-4268 (2009).
Zhang et al., "Ferrous and Cobaltous Chlorides Bearing 2,8-Bis(imino)quinolines: Highly Active Catalysts for Ethylene Polymerization at High Temperature," Organometallics, vol. 29, pp. 1168-1173 (2010).
Zhu et al., "(Py)2Co(CH2SiMe3)2 As an Easily Accessible Source of "CoR2"," Organometallics, 2010, 29 (8), 1897-1908.
Atienza, "Reactivity of Bis(Iminio)Pyridine Cobalt Complexes in C—H Bond Activation and Catalytic C—C and C—Si Bond Formation" PhD thesis, Jun. 2013, Princeton University.
Fernandez et al., "Synthesis and Reactions of Dihydrido(triethylallyl)(1,5-cycloctadiene) -Iridium(III) Complexes: Catalysts for Dehydrogneative Silylation of Alkenese," Organometallics, 1986, 5, 1519-1520.
Albon et al., "Metal Carbonyl Complexes Involving 2,6Bix[I-(phenylimino)ethyl]pyridine: Bidentate Corrdination of a Potentially Tridentate Ligand" Inorganica Chimica Acta, 159 (1989) 19-22.
Bouwkamp, "Iron-Catalyzed [2π+2π] Cycloaddition of α,ω-Dienes the Importance of Redox-Active Supporting Ligands" Journal of the American Chemical Society, 2006, V128 N41, P13340-13341.

\* cited by examiner

REUSABLE HOMOGENEOUS COBALT PYRIDINE DIIMINE CATALYSTS FOR DEHYDROGENATIVE SILYLATION AND TANDEM DEHYDROGENATIVE-SILYLATION-HYDROGENATION

CROSS REFERENCE TO RELATED APPLICATIONS

The present application claims priority to U.S. Provisional Patent Application No. 61/819,761 filed on May 6, 2013, which is incorporated by reference herein in its entirety. This application also claims priority as a continuation-in-part application of U.S. application Ser. No. 13/966,568 filed on Aug. 14, 2013, which claims the benefit of U.S. Provisional Patent Application No. 61/819,753 filed on May 6, 2013 and U.S. Provisional Application No. 61/683,882 filed on Aug. 16, 2012, each of which is incorporated by reference herein in its entirety.

FIELD OF THE INVENTION

This invention relates generally to transition metal-containing compounds, more specifically to cobalt complexes containing pyridine di-imine ligands and their utility as efficient and reusable catalysts for dehydrogenative silylation and tandem dehydrogenative-silylation-hydrogenation.

BACKGROUND OF THE INVENTION

Hydrosilylation chemistry, typically involving a reaction between a silyl hydride and an unsaturated organic group, is the basis for synthetic routes to produce commercial silicone-based products like silicone surfactants, silicone fluids and silanes as well as many addition cured products like sealants, adhesives, and silicone-based coating products. See, for example, US Patent Application Publication 2011/0009573A1 to Delis et al. Typical hydrosilylation reactions use precious metal catalysts to catalyze the addition of a silyl-hydride (Si—H) to an unsaturated group, such as an olefin. In these reactions, the resulting product is a silyl-substituted, saturated compound. In most of these cases, the addition of the silyl group proceeds in an anti-Markovnikov manner, i.e., to the less substituted carbon atom of the unsaturated group. Most precious metal catalyzed hydrosilylations only work well with terminally unsaturated olefins, as internal unsaturations are generally non-reactive or only poorly reactive. There are currently only limited methods for the general hydrosilylation of olefins where after the addition of the Si—H group there still remains an unsaturation in the original substrate. This reaction, termed a dehydrogenative silylation, has potential uses in the synthesis of new silicone materials, such as silanes, silicone fluids, cross-linked silicone elastomers, and silylated or silicone-cross-linked organic polymers such as polyolefins, unsaturated polyesters, and the like.

Various precious metal complex catalysts are known in the art. For example, U.S. Pat. No. 3,775,452 discloses a platinum complex containing unsaturated siloxanes as ligands. This type of catalyst is known as Karstedt's catalyst. Other exemplary platinum-based hydrosilylation catalysts that have been described in the literature include Ashby's catalyst as disclosed in U.S. Pat. No. 3,159,601, Lamoreaux's catalyst as disclosed in U.S. Pat. No. 3,220,972, and Speier's catalyst as disclosed in Speier, J. L, Webster J. A. and Barnes G. H., J. Am. Chem. Soc. 79, 974 (1957).

There are examples of the use of $Fe(CO)_5$ to promote limited hydrosilylations and dehydrogenative silylations. (See Nesmeyanov, A. N.; Freidlina, R. Kh.; Chukovskaya, E. C.; Petrova, R. G.; Belyaysky, A. B. Tetrahedron 1962, 17, 61 and Marciniec, B.; Majchrzak, M. Inorg. Chem. Commun. 2000, 3, 371). The use of $Fe_3(CO)_{12}$ was also found to exhibit dehydrogenative silylation in the reaction of $Et_3SiH$ and styrene. (Kakiuchi, F.; Tanaka, Y.; Chatani, N.; Murai, S. J. Organomet. Chem. 1993, 456, 45). Also, several cyclopentadiene iron complexes have been used to varying degrees of success, with the work of Nakazawa, et al showing interesting intramolecular dehydrogenative silylation/hydrogenation when used with 1,3-di-vinyldisiloxanes. (Roman N Naumov, Masumi Itazaki, Masahiro Kamitani, and Hiroshi Nakazawa, Journal of the American chemical Society, 2012, Volume 134, Issue 2, Pages 804-807)).

A rhodium complex was found to give low to moderate yields of allyl-silanes and vinyl silanes. (Doyle, M. P.; Devora G. A.; Nevadov, A. O.; High, K. G. Organometallics, 1992, 11, 540-555). An iridium complex was also found to give vinyl silanes in good yields. (Falck, J. R.; Lu, B, J. Org Chem, 2010, 75, 1701-1705.) Allyl silanes could be prepared in high yields using a rhodium complex (Mitsudo, T.; Watanabe, Y.; Hori, Y. Bull. Chem. Soc. Jpn. 1988, 61, 3011-3013). Vinyl silanes could be prepared through the use of a rhodium catalyst (Murai, S.; Kakiuchi, F.; Nogami, K.; Chatani, N.; Seki, Y. Organometallics, 1993, 12, 4748-4750). Dehydrogenative silylation was found to occur when iridium complexes were used (Oro, L. A.; Fernandez, M. J.; Esteruelas, M. A.; Jiminez, M. S. J. Mol. Catalysis, 1986, 37, 151-156 and Oro, L. A.; Fernandez, M. J.; Esteruelas, M. A.; Jiminez, M. S. Organometallics, 1986, 5, 1519-1520). Vinyl silanes could also be produced using ruthenium complexes (Murai, S.; Seki, Y.; Takeshita, K.; Kawamoto, K.; Sonoda, N. J. Org. Chem. 1986, 51, 3890-3895.).

A palladium-catalyzed silyl-Heck reaction was recently reported to result in the formation of allyl-silanes and vinyl silanes (McAtee J R, et al., Angewandte Chemie, International Edition in English (Mar. 1, 2012)).

U.S. Pat. No. 5,955,555 discloses the synthesis of certain iron or cobalt pyridine di-imine (PDI) dianion complexes. The preferred anions are chloride, bromide and tetrafluoroborate. U.S. Pat. No. 7,442,819 discloses iron and cobalt complexes of certain tricyclic ligands containing a "pyridine" ring substituted with two imino groups. U.S. Pat. Nos. 6,461,994, 6,657,026 and 7,148,304 disclose several catalyst systems containing certain transitional metal-PDI complexes. U.S. Pat. No. 7,053,020 discloses a catalyst system containing, inter alia, one or more bisarylimino pyridine iron or cobalt catalyst. However, the catalysts and catalyst systems disclosed in these references are described for use in the context of olefin polymerizations and/or oligomerisations, not in the context of dehydrogenative silylation reactions.

Many industrially important homogeneous metal catalysts suffer from the drawback that following consumption of the first charge of substrates, the catalytically active metal is lost to aggregation and agglomeration whereby its catalytic properties are substantially diminished via colloid formation or precipitation. This is a costly loss, especially for noble metals such as Pt. Heterogeneous catalysts are used to alleviate this problem but have limited use for polymers and also have lower activity than homogeneous counterparts. For example, it is well-known in the art and in the hydrosilylation industry that the two primary homogeneous catalysts, Speier's and Karstedt's often lose activity after catalyzing a charge of olefin and silyl- or siloxyhydride reaction. Further, many multistep organic transformations use different catalysts to catalyze separate steps. These catalysts must be tolerant of many species in the mixture, including catalysts used in previous steps, functional groups and by-products. If the number of catalysts could be reduced, and/or if one charge of the homogeneous catalyst could be re-used for multiple charges of substrates via appropriate process design, then cost advantages would be significant. Thus, if products produced via dehydrogenative silylation using one pre-catalyst could also be hydrogenated to saturated products using the active catalyst already present in the mixture, efficiency advantages would be significant, in addition to the flexibility to generate either unsaturated or saturated product classes from one substrate mixture for broader scope of commercial utility.

SUMMARY OF THE INVENTION

In one aspect, the present invention is directed to a process for producing a dehydrogenatively silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenatively silylated product, wherein the catalyst is a complex of the Formula (I) or an adduct thereof;

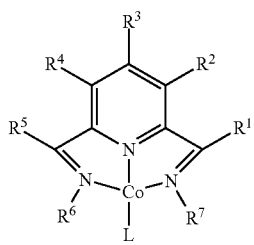

(I)

wherein each occurrence of $R^1$, $R^2$, $R^3$, $R^4$, and $R^5$ is independently hydrogen, C1-C18 alkyl, a C1-C18 substituted alkyl, an aryl, a substituted aryl, or an inert substituent, wherein one or more of $R^1$-$R^5$, other than hydrogen, optionally contain at least one heteroatom; each occurrence of $R^6$ and $R^7$ is independently C1-C18 alkyl, C1-C18 substituted alkyl, aryl or substituted aryl, wherein $R^6$ and $R^7$ optionally contain at least one heteroatom; optionally any two of $R^1$-$R^7$ vicinal to one another, $R^1$-$R^2$, and/or $R^4$-$R^5$ taken together may form a ring being a substituted or unsubstituted, saturated or unsaturated cyclic structure, with the proviso that $R^1$-$R^7$ and $R^8$-$R^6$ are not taken to form a terpyridine ring; and L is hydroxyl, or a C1-C18 alkyl, C1-C18 substituted alkyl, aryl, or substituted aryl group, wherein L optionally contains at least one heteroatom.

In another aspect, the present invention is directed to a compound of Formula (II)

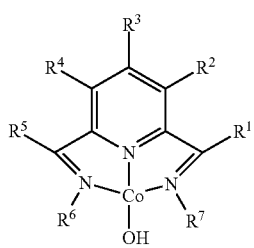

(II)

wherein each occurrence of $R^1$, $R^2$, $R^3$, $R^4$, and $R^5$ is independently hydrogen, C1-C18 alkyl, a C1-C18 substituted alkyl, an aryl, a substituted aryl, or an inert substituent, wherein one or more of $R^1$-$R^5$, other than hydrogen, optionally contain at least one heteroatom; each occurrence of $R^6$ and $R^7$ is independently C1-C18 alkyl, C1-C18 substituted alkyl, aryl or substituted aryl, wherein $R^6$ and $R^7$ optionally contain at least one heteroatom; optionally any two of $R^1$-$R^7$ vicinal to one another, $R^1$-$R^2$, and/or $R^4$-$R^5$ taken together may form a ring being a substituted or unsubstituted, saturated or unsaturated cyclic structure, with the proviso that $R^1$-$R^7$ and $R^8$-$R^6$ are not taken to form a terpyridine ring.

In another aspect, the present invention is directed to a process for producing a crosslinked material, comprising reacting a reaction mixture comprising (a) a silyl-hydride containing polymer, (b) a mono-unsaturated olefin, or an unsaturated polyolefin or mixtures thereof and (c) a catalyst, optionally in the presence of a solvent, in order to produce the crosslinked material, wherein the catalyst is a complex of the Formula (I) or an adduct thereof;

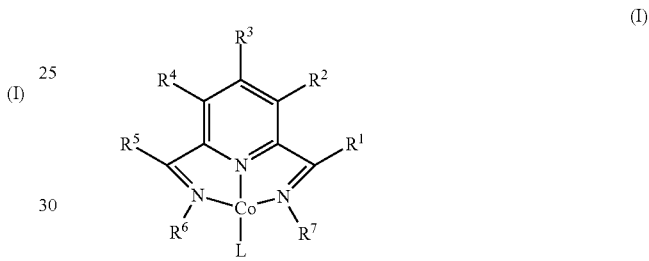

(I)

wherein each occurrence of $R^1$, $R^2$, $R^3$, $R^4$, and $R^5$ is independently hydrogen, C1-C18 alkyl, a C1-C18 substituted alkyl, an aryl, a substituted aryl, or an inert substituent, wherein one or more of $R^1$-$R^5$, other than hydrogen, optionally contain at least one heteroatom; each occurrence of $R^6$ and $R^7$ is independently C1-C18 alkyl, C1-C18 substituted alkyl, aryl or substituted aryl, wherein $R^6$ and $R^7$ optionally contain at least one heteroatom; optionally any two of $R^1$-$R^7$ vicinal to one another, $R^1$-$R^2$, and/or $R^4$-$R^5$ taken together may form a ring being a substituted or unsubstituted, saturated or unsaturated cyclic structure, with the proviso that $R^1$-$R^7$ and $R^8$-$R^6$ are not taken to form a terpyridine ring; and L is hydroxyl, or a C1-C18 alkyl, C1-C18 substituted alkyl, aryl, or substituted aryl group, wherein L optionally contains at least one heteroatom.

In yet another aspect, this invention relates to the reusability of a single charge of catalyst for multiple and sequential charges of the unsaturated substrate and SiH compound for dehydrogenative silylation or for tandem hydrogenation of a dehydrogenatively silylated product formed, without the need for additional charges of catalyst.

DETAILED DESCRIPTION OF THE INVENTION

The invention relates to cobalt complexes containing pyridine di-imine ligands and their use as efficient dehydrogenative silylation and crosslinking catalysts. In one embodiment of the invention, there is provided a complex of the Formulae (I) or (II) as illustrated above, wherein Co in any valence or oxidation state (e.g., +1, +2, or +3) for use in said dehydrogenative silylation and crosslinking reactions. In particular, according to one embodiment of the invention, a class of cobalt pyridine di-imine complexes has been found that are capable of dehydrogenative silylation reactions.

It has now been discovered that less expensive transition metal catalysts based on cobalt-diimine complexes can be reused to catalyze a fresh charge of substrates, or can be re-used to catalyze tandem dehydrogenative-silylation-hydrogentation in the same vessel without the need to isolate or purify the intermediate dehydrogenative silylation product. The stability of the catalysts of the present invention can allow for more efficient industrial silylation processes at lower cost.

By "alkyl" herein is meant to include straight, branched and cyclic alkyl groups. Specific and non-limiting examples of alkyls include, but are not limited to, methyl, ethyl, propyl and isobutyl.

By "substituted alkyl" herein is meant an alkyl group that contains one or more substituent groups that are inert under the process conditions to which the compound containing these groups is subjected. The substituent groups also do not substantially or deleteriously interfere with the process.

By "aryl" herein is meant a non-limiting group of any aromatic hydrocarbon from which one hydrogen atom has been removed. An aryl may have one or more aromatic rings, which may be fused, connected by single bonds or other groups. Specific and non-limiting examples of aryls include, but are not limited to, tolyl, xylyl, phenyl and naphthalenyl.

By "substituted aryl" herein is meant an aromatic group substituted as set forth in the above definition of "substituted alkyl." Similar to an aryl, a substituted aryl may have one or more aromatic rings, which may be fused, connected by single bonds or other groups; however, when the substituted aryl has a heteroaromatic ring, the free valence in the substituted aryl group can be to a heteroatom (such as nitrogen) of the heteroaromatic ring instead of a carbon. If not otherwise stated, it is preferred that substituted aryl groups herein contain 1 to about 30 carbon atoms.

By "alkenyl" herein is meant any straight, branched, or cyclic alkenyl group containing one or more carbon-carbon double bonds, where the point of substitution can be either a carbon-carbon double bond or elsewhere in the group. Specific and non-limiting examples of alkenyls include, but are not limited to, vinyl, propenyl, allyl, methallyl, ethylidenyl norbornane.

By "alkynyl" is meant any straight, branched, or cyclic alkynyl group containing one or more carbon-carbon triple bonds, where the point of substitution can be either at a carbon-carbon triple bond or elsewhere in the group.

By "unsaturated" is meant one or more double or triple bonds. In a preferred embodiment, it refers to carbon-carbon double or triple bonds.

By "inert substituent" herein is meant a group other than hydrocarbyl or substituted hydrocarbyl, which is inert under the process conditions to which the compound containing the group is subjected. The inert substituents also do not substantially or deleteriously interfere with any process described herein that the compound in which they are present may take part in. Examples of inert substituents include halo (fluoro, chloro, bromo, and iodo), ether such as —$OR^8$ wherein $R^8$ is hydrocarbyl or substituted hydrocarbyl.

By "hetero atoms" herein is meant any of the Group 13-17 elements except carbon, and can include for example oxygen, nitrogen, silicon, sulfur, phosphorus, fluorine, chlorine, bromine, and iodine.

By "olefin" herein is meant any aliphatic or aromatic hydrocarbon also containing one or more aliphatic carbon-carbon unsaturations. Such olefins may be linear, branched or cyclic and may be substituted with heteroatoms as described above, with the proviso that the substituents do not interfere substantially or deleteriously with the course of the desired reaction to produce the dehydrogenatively silylated product. In one embodiment, the unsaturated compound useful as a reactant in the dehydrogenative silylation is an organic compound having the structural group, $R_2C\!=\!C\!-\!CHR$, where R is an organic fragment or hydrogen.

As used herein, the term room temperature can refer to a temperature of from about 23° C. to about 30° C.

As indicated above, the present invention is directed to a process for producing a dehydrogenatively silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenative silylated product, wherein the catalyst is a complex of the Formula (I) or an adduct thereof;

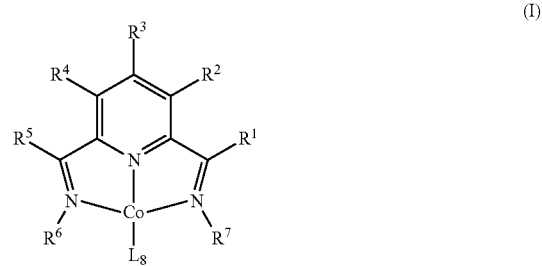

(I)

wherein
each occurrence of $R^1$, $R^2$, $R^3$, $R^4$, and $R^5$ is independently hydrogen, C1-C18 alkyl, a C1-C18 substituted alkyl, an aryl, a substituted aryl, or an inert substituent, wherein one or more of $R^1$-$R^5$, other than hydrogen, optionally contain at least one heteroatom; each occurrence of $R^6$ and $R^7$ is independently C1-C18 alkyl, C1-C18 substituted alkyl, aryl or substituted aryl, wherein $R^6$ and $R^7$ optionally contain at least one heteroatom; optionally any two of $R^1$-$R^7$ vicinal to one another, $R^1$-$R^2$, and/or $R^4$-$R^5$ taken together may form a ring being a substituted or unsubstituted, saturated or unsaturated cyclic structure, with the proviso that $R^1$-$R^7$ and $R^8$-$R^6$ are not taken to form a terpyridine ring; and L is hydroxyl, or a C1-C18 alkyl, C1-C18 substituted alkyl, aryl, or substituted aryl group, wherein L optionally contains at least one heteroatom.

The catalyst utilized in the process of the present invention is illustrated in Formula (I) above wherein Co is in any valence or oxidation state (e.g., +1, +2, or +3). In one embodiment, at least one of $R^6$ and $R^7$ is

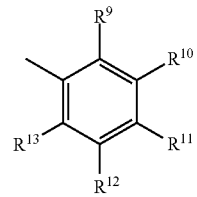

wherein each occurrence of $R^9$, $R^{10}$, $R^{11}$, $R^{12}$, and $R^{13}$ is independently hydrogen, C1-C18 alkyl, C1-C18 substituted alkyl, aryl, substituted aryl, or an inert substituent, wherein $R^9$-$R^{13}$, other than hydrogen, optionally contain at least one heteroatom. $R^9$ and $R^{13}$ may further include independently methyl, ethyl or isopropyl groups and $R^{11}$ may be hydrogen or methyl. In one particularly preferred embodiment, $R^9$, $R^{11}$, and $R^{13}$ are each methyl; $R^1$ and $R^5$ may independently be methyl or phenyl groups; and $R^2$, $R^3$ and $R^4$ may be hydrogen.

One particularly preferred embodiment of the catalyst of the process of the invention is the compound of Formula (II)

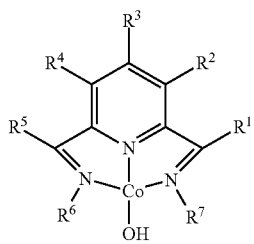

(II)

wherein each occurrence of $R^1$, $R^2$, $R^3$, $R^4$, and $R^5$ is independently hydrogen, C1-C18 alkyl, a C1-C18 substituted alkyl, an aryl, a substituted aryl, or an inert substituent, wherein one or more of $R^1$-$R^5$, other than hydrogen, optionally contain at least one heteroatom; each occurrence of $R^6$ and $R^7$ is independently C1-C18 alkyl, C1-C18 substituted alkyl, aryl or substituted aryl, wherein $R^6$ and $R^7$ optionally contain at least one heteroatom; optionally any two of $R^1$-$R^7$ vicinal to one another, $R^1$-$R^2$, and/or $R^4$-$R^5$ taken together may form a ring being a substituted or unsubstituted, saturated or unsaturated cyclic structure, with the proviso that $R^1$-$R^7$ and $R^8$-$R^6$ are not taken to form a terpyridine ring.

Various methods can be used to prepare the catalyst utilized in the process of the present invention. In one embodiment, the catalyst is generated in-situ by contacting a catalyst precursor with an activator in the presence of a liquid medium containing at least one component selected from the group consisting of a solvent, the silyl hydride, the compound containing at least one unsaturated group, and combinations thereof, wherein the catalyst precursor is represented by structural Formula (III)

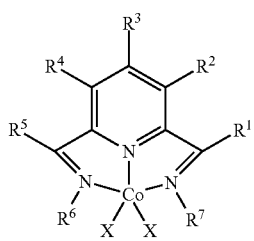

(III)

wherein each occurrence of $R^1$, $R^2$, $R^3$, $R^4$, and $R^5$ is independently hydrogen, C1-C18 alkyl, a C1-C18 substituted alkyl, an aryl, a substituted aryl, or an inert substituent, wherein one or more of $R^1$-$R^5$, other than hydrogen, optionally contain at least one heteroatom; each occurrence of $R^6$ and $R^7$ is independently C1-C18 alkyl, C1-C18 substituted alkyl, aryl or substituted aryl, wherein $R^6$ and $R^7$ optionally contain at least one heteroatom; optionally any two of $R^1$-$R^7$ vicinal to one another, $R^1$-$R^2$, and/or $R^4$-$R^5$ taken together may form a ring being a substituted or unsubstituted, saturated or unsaturated cyclic structure, with the proviso that $R^1$-$R^7$ and $R^8$-$R^6$ are not taken to form a terpyridine ring; and X is an anion selected from the group consisting of $F^-$, $Cl^-$, $Br^-$, $I^-$, $CF_3R^{14}SO_3^-$ or $R^{15}COO^-$, wherein $R^{14}$ is a covalent bond or a C1-C6 alkylene group, and $R^{15}$ is a C1-C10 substituted or unsubstituted hydrocarbyl group.

The activator may be a reducing agent or an alkylating agent such as $NaHBEt_3$, $CH_3Li$, DIBAL-H, LiHMDS, a Grignard reagent as well as combinations thereof. Preferably, the reducing agent has a reduction potential more negative than −0.6 v (versus ferrocene, as described in Chem. Rev. 1996, 96, 877-910. A larger negative number represents a larger reduction potential). Preferably, the reduction potential ranges from −0.76 V to −2.71V. The most preferred reducing agents have a reduction potential in the range of −2.8 to −3.1 V.

The methods to prepare the catalysts are known to a person skilled in the field. For example, the catalysts can be prepared by reacting a PDI ligand with a metal halide, such as $FeBr_2$ as disclosed in US Patent Application Publication 2011/0009573A1. Typically, the PDI ligands are produced through condensation of an appropriate amine or aniline with 2,6-diacetylpyridine and its derivatives. If desired, the PDI ligands can be further modified by known aromatic substitution chemistry.

In the process of the invention, the catalysts can be unsupported or immobilized on a support material, for example, carbon, silica, alumina, $MgCl_2$ or zirconia, or on a polymer or prepolymer, for example polyethylene, polypropylene, polystyrene, poly(aminostyrene), or sulfonated polystyrene. The metal complexes can also be supported on dendrimers.

In some embodiments, for the purposes of attaching the metal complexes of the invention to a support, it is desirable that at least one of $R^1$ to $R^7$ of the metal complexes has a functional group that is effective to covalently bond to the support. Exemplary functional groups include but are not limited to SH, COOH, $NH_2$ or OH groups.

In one embodiment, silica supported catalyst may be prepared via Ring-Opening Metathesis Polymerization (ROMP) technology as discussed in the literature, for example Macromol. Chem. Phys. 2001, 202, No. 5, pages 645-653; Journal of Chromatography A, 1025 (2003) 65-71.

One way to immobilize catalysts on the surface of dendrimers is by the reaction of Si—Cl bonded parent dendrimers and functionalized PDI in the presence of a base is as illustrated by Kim et al. in Journal of Organometallic Chemistry 673 (2003) 77-83.

The unsaturated compound containing at least one unsaturated functional group utilized in the process of the invention can be a compound having one, two, three, or more unsaturations. Examples of such unsaturated compounds include an olefin, a cycloalkene, unsaturated polyethers such as an alkyl-capped allyl polyether, a vinyl-functional alkyl-capped allyl or methallyl polyether, an alkyl-capped terminally unsaturated amine, an alkyne, terminally unsaturated acrylate or methacrylate, unsaturated aryl ether, vinyl-functionalized polymer or oligomer, vinyl-functionalized silane, vinyl-functionalized silicone, unsaturated fatty acids, unsaturated esters, and combinations thereof.

Unsaturated polyethers suitable for the dehydrogenative silylation reaction preferably are polyoxyalkylenes having the general formula:

$$R^{16}(OCH_2CH_2)_z(OCH_2CHR^3)_w\!-\!OR^{17} \quad \text{(Formula IV) or}$$

$$R^{17}O(CHR^{18}CH_2O)_w(CH_2CH_2O)_z\!-\!CR^{19}_2\!-\!C\!\equiv\!C\!-\!CR^{19}_2\!-\!(OCH_2CH_2)_z(OCH_2CHR^3)_wR^2 \quad \text{(Formula V) or}$$

$$H_2C\!=\!CR^{19}CH_2\!-\!O\!-\!(CH_2CH_2O)_z(CH_2CHR^{18}O)_wCH_2CR^{19}\!=\!CH_2 \quad \text{(Formula VI)}$$

wherein $R^{16}$ denotes an unsaturated organic group containing from 2 to 10 carbon atoms such as allyl, methylallyl, propargyl or 3-pentynyl. When the unsaturation is olefinic, it is desirably terminal to facilitate smooth dehydrogenative silylation. However, when the unsaturation is a triple bond, it may be internal. $R^{17}$ is hydrogen, vinyl, or a polyether capping group of from 1 to 8 carbon atoms such as the alkyl groups: $CH_3$, $n\text{-}C_4H_9$, $t\text{-}C_4H_9$ or $i\text{-}C_8H_{17}$, the acyl groups such as $CH_3COO$, $t\text{-}C_4H_9COO$, the beta-ketoester group such as $CH_3C(O)CH_2C(O)O$, or a trialkylsilyl group. $R^{18}$ and $R^{19}$ are monovalent hydrocarbon groups such as the C1-C20 alkyl groups, for example, methyl, ethyl, isopropyl, 2-ethylhexyl, dodecyl and stearyl, or the aryl groups, for example, phenyl and naphthyl, or the alkaryl or aralkyl groups, for example, benzyl, phenylethyl and nonylphenyl, or the cycloalkyl groups, for example, cyclohexyl and cyclooctyl. $R^{19}$ may also be hydrogen. Methyl is the most preferred $R^{18}$ and $R^{19}$ groups. Each occurrence of z is 0 to 100 inclusive and each occurrence of w is 0 to 100 inclusive. Preferred values of z and w are 1 to 50 inclusive.

Specific examples of preferred unsaturated compounds useful in the process of the present invention include N,N-dimethylallyl amine, allyloxy-substituted polyethers, propylene, 1-butene, 1-hexene, styrene, vinylnorbornane, 5-vinyl-norbornene, long-chain, linear alpha olefins such as 1-octadecene, internal olefins such as cyclopentene, cyclohexene, norbornene, and 3-hexene, branched olefins such as isobutylene and 3-methyl-1-octene, unsaturated polyolefins, e.g., polybutadiene, polyisoprene and EPDM, unsaturated acids or esters such as oleic acid, linoleic acid and methyl oleate, a vinyl siloxane of the Formula (VII), and combinations thereof, wherein Formula (VII) is

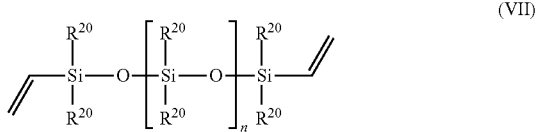

(VII)

wherein each occurrence of $R^{20}$ is independently a C1-C18 alkyl, C1-C18 substituted alkyl, vinyl, C3-C18 terminal alkenyl, aryl, or a substituted aryl, and n is greater than or equal to zero. As defined herein, "internal olefin" means an olefin group not located at a chain or branch terminus, such as 3-hexene.

The silyl hydride employed in the reaction is not particularly limited. It can be any compound selected from the group consisting of $R_aSiR_{4-a}$, $(RO)_aSiR_{4-a}$, $Q_uT_vT_p^H D_wD^H_xM^H_yM_z$, and combinations thereof. The silyl hydride can contain linear, branched or cyclic structures, or combinations thereof. As used herein, each occurrence of R is independently C1-C18 alkyl, C1-C18 substituted alkyl, wherein R optionally contains at least one heteroatom, each occurrence of a independently has a value from 1 to 3, each of p, u, v, y and z independently has a value from 0 to 20, w and x are from 0 to 500, provided that p+x+y equals 1 to 500 and the valences of the all the elements in the silyl hydride are satisfied. Preferably, p, u, v, y, and z are from 0 to 10, w and x are from 0 to 100, wherein p+x+y equals 1 to 100.

As used herein, an "M" group represents a monofunctional group of formula $R'_3SiO_{1/2}$, a "D" group represents a difunctional group of formula $R'_2SiO_{2/2}$, a "T" group represents a trifunctional group of formula $R'SiO_{3/2}$, and a "Q" group represents a tetrafunctional group of formula $SiO_{4/2}$, an "$M^H$" group represents $HR'_2SiO_{1/2}$, a "$T^H$" represents $HSiO_{3/2}$, and a "$D^H$" group represents $R'HSiO_{2/2}$. Each occurrence of R' is independently C1-C18 alkyl, C1-C18 substituted alkyl, wherein R' optionally contains at least one heteroatom.

Examples of silyl hydrides containing at least one silyl-hydride functional group include $R_aSiR_{4-a}$, $(RO)_aSiH_{4-a}$, $HSiR_a(OR)_{3-a}$, $R_3Si(CH_2)_f(SiR_2O)_kSiR_2H$, $(RO)_3Si(CH_2)_f(SiR_2O)_kSiR_2H$, $Q_uT_vT_p^H D_wD^H_xM^H_yM_z$, and combinations thereof, wherein Q is $SiO_{4/2}$, T is $R'SiO_{3/2}$, $T^H$ is $HSiO_{3/2}$, D is $R'_2SiO_{2/2}$, $D^H$ is $R'HSiO_{2/2}$, $M^H$ is $HR'_2SiO_{1/2}$, $M^H$ is $R'_3SiO_{1/2}$, each occurrence of R and R' is independently C1-C18 alkyl, C1-C18 substituted alkyl, aryl, or substituted aryl, wherein R and R' optionally contain at least one heteroatom, each occurrence of a independently has a value from 1 to 3, f has a value of 1 to 8, k has a value of 1 to 11, p is from 0 to 20, u is from 0 to 20, v is from 0 to 20, w is from 0 to 1000, x is from 0 to 1000, y is from 0 to 20, and is from 0 to 20, provided that p+x+y equals 1 to 3000, and the valences of the all the elements in the silyl hydride are satisfied. In the above formulations, p, u, v, y, and z may also be from 0 to 10, w and x may be from 0 to 100, wherein p+x+y equals 1 to 100.

In one embodiment, the silyl hydride has one of the following structures:

(Formula VIII)

(Formula IX)

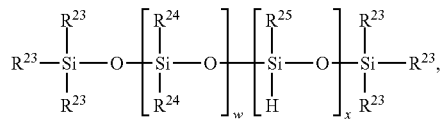

(Formula X)

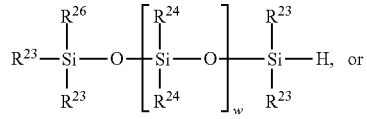

(Formula XI)

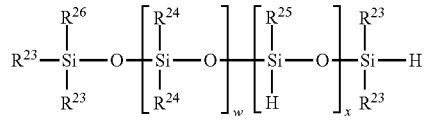

wherein each occurrence of $R^{21}$, $R^{22}$, $R^{23}$, $R^{24}$, and $R^{25}$ is independently a C1-C18 alkyl, C1-C18 substituted alkyl, aryl, or substituted aryl, $R^{26}$ is hydrogen, a C1-C18 alkyl, C1-C18 substituted alkyl, aryl, or substituted aryl, x and w are independently greater than or equal to 0 (x is at least equal to 1 for Formula IX)), and a and b are integers from 0 to 3 provided that a+b=3.

The catalysts of the invention are useful for catalyzing dehydrogenative silylation reactions. For example, when an appropriate silyl hydride, such as triethoxysilane, triethylsilane, $MD^HM$, or a silyl-hydride functional polysiloxane (SL 6020 from Momentive Performance Materials, Inc., for example) are reacted with a mono-unsaturated hydrocarbon, such as octene, dodecene, butene, etc, in the presence of the Co catalyst, the resulting product is a terminally-silyl-substituted alkene, where the unsaturation is in a beta position relative to the silyl group. A by-product of this reaction is the hydrogenated olefin. When the reaction is performed with a molar ratio of silane to olefin of 0.5:1, the resulting products are formed in a 1:1 ratio. An example is shown in the reaction scheme below.

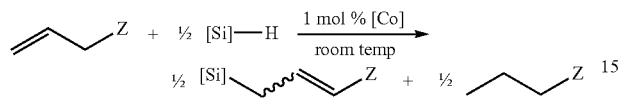

The reactions are typically facile at ambient temperatures and pressures, but can also be run at lower or higher temperatures (0 to 300° C.) or pressures (ambient to 3000 psi). A range of unsaturated compounds can be used in this reaction, such as N,N-dimethylallyl amine, allyloxy-substituted polyethers, cyclohexene, and linear alpha olefins (i.e., 1-butene, 1-octene, 1-dodecene, etc.). When an alkene containing internal double bonds is used, the catalyst is capable of first isomerizing the olefin, with the resulting reaction product being the same as when the terminally-unsaturated alkene is used.

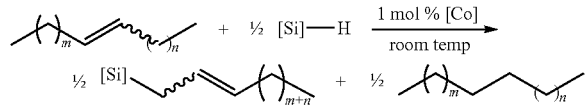

If the reaction is run with a 1:1 silyl-hydride to olefin ratio, the reaction can give a bis-substituted silane, where the silyl groups are in the terminal positions of the compound, and there is still an unsaturated group present in the product.

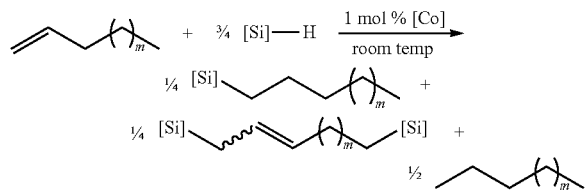

If the catalyst is first used to prepare a terminally-substituted silyl-alkene, a second silane may be added to produce an asymmetrically substituted bis-silyl alkene. The resulting silane is terminally substituted at both ends. This bis-silane can be a useful starting material for the production of alpha,omega-substituted alkanes or alkenes, such as diols and other compounds easily derived from the silylated product. Long chain alpha,omega-substituted alkanes or alkenes are not easily prepared today, and could have a variety of uses for preparing unique polymers (such as polyurethanes) or other useful compounds.

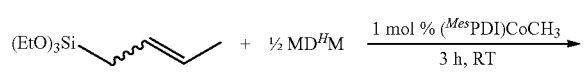

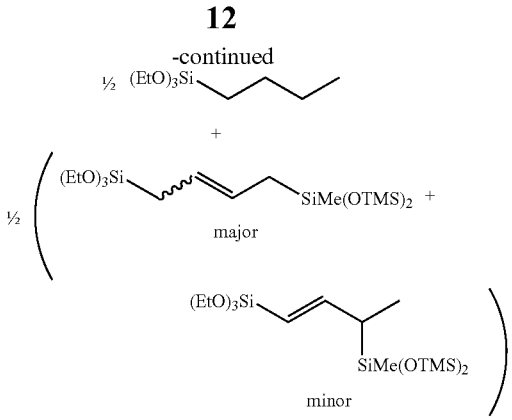

Because the double bond of an alkene is preserved during the dehydrogenative silylation reaction employing these cobalt catalysts, a singly-unsaturated olefin may be used to crosslink silyl-hydride containing polymers. For example, a silyl-hydride polysiloxane, such as SL6020 ($MD_{15}D^H_{30}M$), may be reacted with 1-octene in the presence of the cobalt catalysts of this invention to produce a crosslinked, elastomeric material. A variety of new materials can be produced by this method by varying the hydride polymer and length of the olefin used for the crosslinking. Accordingly, the catalysts used in the process of the invention have utility in the preparation of useful silicone products, including, but not limited to, coatings, for example release coatings, room temperature vulcanizates, sealants, adhesives, products for agricultural and personal care applications, and silicone surfactants for stabilizing polyurethane foams.

Additionally, this invention also provides for tandem hydrogenation of the unsaturated product to saturated species simply via introducing hydrogen gas into the reaction vessel following the dehydrogenative silylation reaction.

Furthermore, the dehydrogenative silylation may be carried out on any of a number of unsaturated polyolefins, such as polybutadiene, polyisoprene or EPDM-type copolymers, to either functionalize these commercially important polymers with silyl groups or crosslink them via the use of hydrosiloxanes containing multiple SiH groups at lower temperatures than conventionally used. This offers the potential to extend the application of these already valuable materials in newer commercially useful areas.

In one embodiment, the catalysts are useful for dehydrogenative silylation of a composition containing a silyl hydride and a compound having at least one unsaturated group. The process includes contacting the composition with a metal complex of the catalyst, either supported or unsupported, to cause the silyl hydride to react with the compound having at least one unsaturated group to produce a dehydrogenative silylation product, which may contain the metal complex catalyst. The dehydrogenative silylation reaction can be conducted optionally in the presence of a solvent. If desired, when the dehydrogenative silylation reaction is completed, the metal complex can be removed from the reaction product by magnetic separation and/or filtration. These reactions may be performed neat, or diluted in an appropriate solvent. Typical solvents include benzene, toluene, diethyl ether, etc. It is preferred that the reaction is performed under an inert atmosphere. The catalyst can be generated in-situ by reduction using an appropriate reducing agent.

The catalyst complexes of the invention are efficient and selective in catalyzing dehydrogenative silylation reactions. For example, when the catalyst complexes of the invention are employed in the dehydrogenative silylation of an alkyl-capped allyl polyether or a compound containing an unsaturated group, the reaction products are essentially free of unreacted alkyl-capped allyl polyether and its isomerization products. In one embodiment, the reaction products do not contain the unreacted alkyl-capped allyl polyether and its isomerization products. Further, when the compound containing an unsaturated group is an unsaturated amine compound, the dehydrogenatively silylated product is essentially free of internal addition products and isomerization products of the unsaturated amine compound. As used herein, "essentially free" is meant no more than 10 wt %, preferably 5 wt % based on the total weight of the hydrosilylation product. "Essentially free of internal addition products" is meant that silicon is added to the terminal carbon.

In addition to the above catalytic processes, it has been discovered that the catalysts of the present invention offer two additional advantages. First, the catalysts of the present invention are not destroyed during the catalytic processes outlined above. The stability of these catalysts allows them to be used multiple times without loss of catalytic activity. For example, in one embodiment, it is possible to use the catalysts of the present invention to perform dehydrogenative silylation of a composition containing a silyl hydride and a compound having at least one unsaturated group as described above, and then subsequently add fresh reactants to the reaction vessel and continue the dehydrogenative silylation reaction using the same catalyst. Second, the catalysts of the present invention can be re-used to catalyze tandem dehydrogenative-silylation-hydrogentation in the same vessel without the need to isolate or purify the intermediate dehydrogenative silylation product. For example, in one embodiment, it is possible to use the catalysts of the present invention to perform dehydrogenative silylation of a composition containing a silyl hydride and a compound having at least one unsaturated group as described above, and then subsequently add hydrogen gas directly to the reaction vessel to effect a hydrogenation reaction using the same catalyst. This allows the flexibility to generate a dehydrogenatively silylated product or a saturated product in the same vessel without the need to transfer to another vessel or use another catalyst.

The catalyst loading can be chosen as desired for a particular purpose or intended application. In one embodiment, the catalyst is present in an amount of from about 0.1 mol % to about 5 mol %; from about 0.5 mol % to about 3 mol %; even from about 1 mol % to about 5 mol %. Here as elsewhere in the specification and claims, numerical values can be combined to form new and non-disclosed or non-specified ranges. The catalyst loadings expressed as mol % of the cobalt complex are based on the moles of cobalt complex in relation to the moles of unsaturated compound and can be evaluated expressed by ($mol_{Co\ complex}/mol_{olefin} \times 100$).

The following examples are intended to illustrate, but in no way limit the scope of the present invention. All parts and percentages are by weight and all temperatures are in degrees Celsius unless explicitly stated otherwise. All the publications and the US patents referred to in the application are hereby incorporated by reference in their entireties.

EXAMPLES

General Considerations

All air- and moisture-sensitive manipulations were carried out using standard vacuum line, Schlenk, and cannula techniques or in an MBraun inert atmosphere dry box containing an atmosphere of purified nitrogen. Solvents for air- and moisture-sensitive manipulations were initially dried and deoxygenated using literature procedures (Pangborn, A B et al., to Organometallics 15:1518 (1996)). Chloroform-d and benzene-$d_6$ were purchased from Cambridge Isotope Laboratories. The complexes ($^{iPr}$PDI)CoN$_2$, (Bowman A C et al., JACS 132:1676 (2010)), ($^{Et}$PDI)CoN$_2$, (Bowman A C et al., JACS 132:1676 (2010)), ($^{iPr}$PDI)CoN$_2$, (Bowman A C et al., JACS 132:1676 (2010)), ($^{Mes}$PDI)CoCH$_3$ (Humphries, M J Organometallics 24:2039.2 (2005)), ($^{Mes}$PDI)CoCl, (Humphries, M J Organometallics 24:2039.2 (2005)) [($^{Mes}$PDI)CoN$_2$][MeB(C$_6$F$_5$)$_3$] (Gibson, V C et al., J. Chem. Comm. 2252 (2001)), and [($^{Mes}$PDI)CoCH$_3$][BArF$_{24}$] (Atienza, C C H et al., Angew. Chem. Int. Ed. 50:8143 (2011)) were prepared according to reported literature procedures. Bis(trimethylsiloxy)methylsilane (MD$^H$M), (EtO)$_3$SiH and Et$_3$SiH were acquired from Momentive Performance Materials and were distilled from calcium hydride before use. The substrates, 1-octene (TCI America), tert-butylethylene or TBE (Alfa Aesar), N,N-dimethylallylamine (TCI America) and styrene (Alfa Aesar) were dried on calcium hydride and distilled under reduced pressure before use. 1-Butene (TCI America), allylamine (Alfa Aesar) and allylisocyanate (Alfa Aesar) were dried over 4 Å molecular sieves. SilForce® SL6100 (M$^{vi}$D$_{120}$M$^{vi}$), SilForce® SL6020 (MD$_{15}$D$^H_{30}$M) and the allyl polyethers were acquired from Momentive Performance Materials and dried under high vacuum for 12 hours before use.

$^1$H NMR spectra were recorded on Inova 400 and 500 spectrometers operating at 399.78, and 500.62 MHz, respectively. $^{13}$C NMR spectra were recorded on an Inova 500 spectrometer operating at 125.893 MHz. All $^1$H and $^{13}$C NMR chemical shifts are reported relative to SiMe$_4$ using the $^1$H (residual) and $^{13}$C chemical shifts of the solvent as a secondary standard. The following abbreviations and terms are used: bs—broad singlet; s—singlet; t—triplet; bm—broad multiplet; GC—Gas Chromatography; MS—Mass Spectroscopy; THF—tetrahydrofuran GC analyses were performed using a Shimadzu GC-2010 gas chromatograph equipped with a Shimadzu AOC-20s autosampler and a Shimadzu SHRXI-5MS capillary column (15 m×250 μm). The instrument was set to an injection volume of 1 μL, an inlet split ratio of 20:1, and inlet and detector temperatures of 250° C. and 275° C., respectively. UHP-grade helium was used as carrier gas with a flow rate of 1.82 mL/min. The temperature program used for all the analyses is as follows: 60° C., 1 min; 15° C./min to 250° C., 2 min.

Catalyst loadings in the following text are reported in mol % of the cobalt complex ($mol_{Co\ complex}/mol_{olefin} \times 100$).

Example 1

Synthesis of ($^{Mes}$PDI)CoN$_2$

This compound was prepared in a manner similar to the synthesis of ($^{iPr}$PDI)CoN$_2$ (Bowman, supra) with 0.500 g (0.948 mmol) of ($^{Mes}$PDI)CoCl$_2$, 0.110 g (4.75 mmol, 5.05 equiv) of sodium and 22.0 g (108 mmol, 114 equiv) of mercury. Recrystallization from 3:1 pentane/toluene yielded 0.321 g (70%) of very dark teal crystals identified as ($^{Mes}$PDI)CoN$_2$. Analysis for C$_{27}$H$_{31}$N$_5$Co: Calc. C, 66.93; H, 6.45; N, 14.45. Found. C, 66.65; H, 6.88; N, 14.59. $^1$H NMR (benzene-$d_6$): 3.58 (15 Hz), 4.92 (460 Hz). IR (benzene): $\nu_{NN}$=2089 cm$^{-1}$.

Example 2

Synthesis of ($^{Mes}$PDI)CoOH

A 20 mL scintillation vial was charged with 0.100 g (0.203 mmol) of ($^{Mes}$PDI)CoCl, 0.012 g (0.30 mmol, 1.5 equiv) of NaOH, and approximately 10 mL THF. The reaction was stirred for two days upon which the color of the solution changed from dark pink to red. THF was removed in vacuo and the residue was dissolved in approximately 20 mL toluene. The resulting solution was filtered through Celite and the solvent was removed from the filtrate in vacuo. Recrystallization of the crude product from 3:1 pentane/toluene yielded 0.087 g (90%) of dark pink crystals identified as ($^{Mes}$PDI)CoOH. The compound is dichroic in solution exhibiting a pink color with a green hue. Analysis for $C_{27}H_{32}CoN_3O$: Calc. C, 68.49; H, 6.81; N, 8.87. Found. C, 68.40; H, 7.04; N, 8.77. $^1$H NMR (benzene-$d_6$): δ=0.26 (s, 6H, C(CH$_3$)), 1.07 (s, 1H, CoOH), 2.10 (s, 12H, o-CH$_3$), 2.16 (s, 6H, p-CH$_3$), 6.85 (s, 4H, m-aryl), 7.49 (d, 2H, m-pyridine), 8.78 (t, 1H, p-pyridine). $^{13}$C {$^1$H} NMR (benzene-$d_6$): δ=19.13 (o-CH$_3$), 19.42 (C(CH$_3$)), 21.20 (p-CH$_3$) 114.74 (p-pyridine), 121.96 (m-pyridine), 129.22 (m-aryl), 130.71 (o-aryl), 134.78 (p-aryl), 149.14 (i-aryl), 153.55 (o-pyridine), 160.78 (C=N). IR (benzene): $\upsilon_{OH}$=3582 cm$^{-1}$.

Example 3

Silylation of 1-Octene with MD$^H$M Using Various Co Complexes

In a nitrogen-filled drybox, a scintillation vial was charged with 0.100 g (0.891 mmol) of 1-octene and 0.009 mmol (1 mol %) of the cobalt complex (see Table 1 for specific amounts). 0.100 g (0.449 mmol, 0.50 equiv) of MD$^H$M was then added to the mixture and the reaction was stirred at room temperature for one hour/24 hours. The reaction was quenched by exposure to air and the product mixture was analyzed by gas chromatography and NMR spectroscopy.

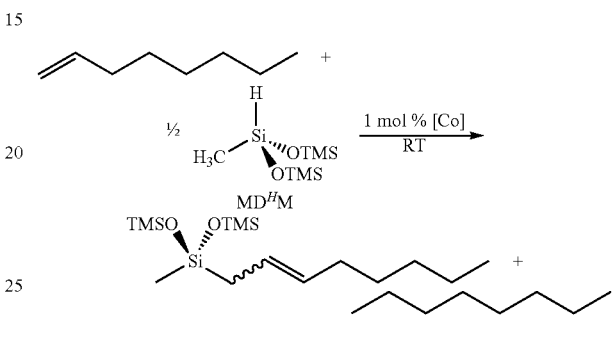

TABLE 1

| | | 1 hr | | | 24 hrs | | |
|---|---|---|---|---|---|---|---|
| Catalyst | Amount | % conv | % silylated pdt | % octane | % conv | % silylated pdt | % octane |

Catalyst screening for the silylation of 1-octene with MD$^H$M.*

| | Catalyst | Amount | % conv | % silylated pdt | % octane | % conv | % silylated pdt | % octane |
|---|---|---|---|---|---|---|---|---|
| 3A | | 5 mg (0.009 mmol) | Trace | — | — | 39 | 19 | 20 |
| 3B | | 6 mg (0.009 mmol) | Trace | — | — | 46 | 23 | 23 |

TABLE 1-continued

Catalyst screening for the silylation of 1-octene with $MD^HM$.*

| | | | 1 hr | | | 24 hrs | | |
|---|---|---|---|---|---|---|---|---|
| Catalyst | | Amount | % conv | % silylated pdt | % octane | % conv | % silylated pdt | % octane |
| 3C | | 4 mg (0.008 mmol) | 87 | 47 | 40 | >98 | 52 | 46 |
| 3D | | 4 mg (0.008 mmol) | >98 | 46 | 52 | — | — | — |
| 3E | | 4 mg (0.008 mmol) | >98 | 49 | 49 | — | — | — |
| 3F | | 4 mg (0.008 mmol) | 65 | 35 | 30 | >98 | 49 | 49 |

TABLE 1-continued

Catalyst screening for the silylation of 1-octene with $MD^HM$.*

| | | | 1 hr | | | 24 hrs | |
| --- | --- | --- | --- | --- | --- | --- | --- |
| Catalyst | | Amount | % conv | % silylated pdt | % octane | % conv | % silylated pdt | % octane |
| 3G | [structure with BArF$_{24}$, Co, CH$_3$, Ar] | 12 mg (0.009 mmol) | Trace | — | — | 32 | 16 | 16 |

*% Conversion and product distribution determined by GC-FID. % octane and % silylated product are reported as percentages of the compounds in the reaction mixture.

Example 4

Silylation of 1-Octene with Different Silanes Using ($^{Mes}$PDI)CoCH$_3$ and ($^{Mes}$PDI)CoN$_2$ In a nitrogen-filled drybox, a scintillation vial was charged with 0.100 g (0.891 mmol) of 1-octene and 0.009 mmol (1 mol %) of the cobalt complex [0.004 g ($^{Mes}$PDI)CoCH$_3$ or 0.004 g ($^{Mes}$PDI)CoN$_2$]. 0.449 mmol (0.5 equiv) of the silane (0.100 g $MD^HM$, 0.075 g (EtO)$_3$SiH or 0.052 g Et$_3$SiH) was then added to the mixture and the reaction was stirred at room temperature for the desired amount of time. The reaction was quenched by exposure to air and the product mixture was analyzed by gas chromatography and NMR spectroscopy. Results are shown in Table 2

TABLE 2

Silylation of 1-octene with various silanes.*

| Catalyst | Silane | Time | % conv | % silylated pdt | % octane |
| --- | --- | --- | --- | --- | --- |
| [structure with Co-CH$_3$] | $MD^HM$ | 15 min | >98 | 49 | 49 |
| | (EtO)$_3$SiH | 15 min | >98 | 43 | 55 |
| | Et$_3$SiH | 24 hrs | >98 | 46 | 52 |
| [structure with Co-N$_2$] | $MD^HM$ | 30 min | >98 | 46 | 52 |
| | (EtO)$_3$SiH | 15 min | >98 | 45 | 53 |
| | Et$_3$SiH | 24 hrs | 88 | 45 | 43 |

*% Conversion and product distribution determined by GC-FID. % octane and % silylated product are reported as percentages of the compounds in the reaction mixture.

Example 5

In Situ Activation of Cobalt Pre-Catalysts

A 20 mL scintillation vial was charged with 0.100 g (0.891 mmol) of 1-octene, 0.100 g (0.449 mmol) MD$^H$M and 0.005 g (0.009 mmol, 1 mol %) of ($^{Mes}$PDI)CoCl$_2$. 0.019 mmol (2 mol %) of the activator (0.019 mL of 1.0 M NaHBEt$_3$ in toluene; 0.012 mL of 1.6 M CH$_3$Li in diethyl ether; 0.019 mL of 1.0 M DIBAL-H in toluene; 0.003 g LiHMDS) was then added to the mixture and the reaction was stirred for 1 hour at room temperature. The reaction was quenched by exposure to air followed by analysis of the mixture by GC. In all cases, full conversion of 1-octene to an approximately 1:1 mixture of 1-bis(trimethylsiloxy)methylsilyl-2-octene and octane was observed.

Example 6

Silylation of Cis- and Trans-4-Octene with Different Silanes Using ($^{Mes}$PDI)CoCH$_3$ The reactions were carried out in a manner similar to silylation of 1-octene using 0.100 g (0.891 mmol) of cis- or trans-4-octene and 0.009 mmol (1 mol %) of the cobalt complex (0.004 g of ($^{Mes}$PDI)CoCH$_3$), and 0.629 mmol (0.5 equiv) of the silane (0.100 g MD$^H$M, 0.075 g (EtO)$_3$SiH or 0.052 g Et$_3$SiH). The reactions were stirred at room temperature for 24 hours and then quenched by exposure to air and the product mixtures were analyzed by gas chromatography and NMR spectroscopy. Results are shown in Table 3.

TABLE 3

Silylation of cis- and trans-4-octene with various silanes.*

| Olefin | Silane | % conv | % silylated pdt** | % octane |
|---|---|---|---|---|
| cis-4-octene | MD$^H$M | >98 | 51 (88% C$_1$) | 47 |
|  | (EtO)$_3$SiH |  | intractable mixture |  |
|  | Et$_3$SiH | 70 | 35 (75% C$_1$) | 35 |
| trans-4-octene | MD$^H$M | >98 | 53 (93% C$_1$) | 45 |
|  | (EtO)$_3$SiH |  | intractable mixture |  |
|  | Et$_3$SiH | 85 | 39 (72% C$_1$) | 46 |

*% Conversion and product distribution determined by GC-FID. % octane and % silylated product are reported as percentages of the compounds in the reaction mixture.
**Values in parentheses are % 1-silyl-2-octene product.

Example 7

Silylation of 1-Octene with MD$^H$M Using ($^{Mes}$PDI)CoCH$_3$ in the Presence of H$_2$ In a nitrogen-filled drybox, a thick-walled glass vessel was charged with 0.200 g (1.78 mmol) of 1-octene and 0.400 g (1.80 mmol) of MD$^H$M. The solution was frozen in the cold well and 0.008 g (0.017 mmol, 1 mol %) of ($^{Mes}$PDI)CoCH$_3$ was added on the surface of the frozen solution. The reaction vessel was quickly capped, brought out of the drybox and placed in a Dewar filled with liquid nitrogen to keep the solution frozen. The vessel was degassed and approximately 1 atm of H$_2$ was admitted. The solution was thawed and stirred at room temperature for one hour. The reaction was quenched by opening the glass vessel to air. Analysis of the product mixture by GC showed >98% conversion of 1-octene to octane (74%) and 1-bis(trimethylsiloxy)methylsilyloctane (24%).

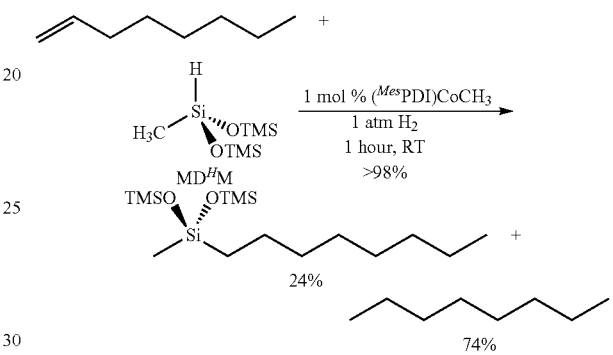

Example 8

Silylation of 1-Butene with Different Silanes Using ($^{Mes}$PDI)CoCH$_3$

A thick-walled glass vessel was charged with 0.449 mmol of the silane (0.100 g MD$^H$M, 0.075 g (EtO)$_3$SiH or 0.052 g Et$_3$SiH) and 0.004 g (0.009 mmol) of ($^{Mes}$PDI)CoCH$_3$. The mixture was frozen in liquid nitrogen and the reaction vessel was degassed. 0.891 mmol of 1-butene was admitted into the vessel using a calibrated gas bulb. The mixture was thawed and stirred at room temperature for 1 hour. The volatiles were distilled into a J. Young tube containing CDCl$_3$ and analyzed by NMR spectroscopy. The remaining residue was exposed to air and analyzed by GC and NMR spectroscopy. Results are shown in Table 4.

TABLE 4

Silylation of 1-butene with various silanes.*

| Catalyst | Silane | % conv | cis isomer | trans isomer | Volatiles |
|---|---|---|---|---|---|
|  | MD$^H$M | >95 | 52 | 48 | butane |
|  | (EtO)$_3$SiH | >95 | 32 | 68 | butane |
|  | Et$_3$SiH | <5 | — | — | 1-butene |

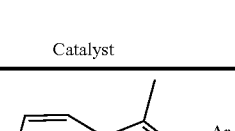

*% Conversion and product distribution determined by GC and $^1$H NMR spectroscopy.

Characterization of Products

1-bis(trimethylsiloxy)methylsilyl-2-butene $^1$H NMR (CDCl$_3$): δ=0.00 and 0.01 (s, 2×3H, (OTMS)$_2$SiCH$_3$), 0.08 and 0.09 (s, 2×18H, OSi(CH$_3$)$_3$), 1.38 and 1.45 (d, 2×2H, SiCH$_2$CH=CH), 1.57 and 1.64 (d, 2×3H, CH=CHCH$_3$), 5.25 to 5.43 (m, 4×1H, CH=CH). $^{13}$C {$^1$H} NMR (CDCl$_3$): δ=−0.44 and −0.60 ((OTMS)$_2$SiCH$_3$); 1.98 (OSi(CH$_3$)$_3$); 18.27 (CH=CHCH$_3$); 19.19 and 23.71 (SiCH$_2$CH=CH); 122.17, 124.12, 125.34, 126.09 (CH=CH).

1-triethoxysilyl-2-butene $^1$H NMR (CDCl$_3$): δ=1.21 (t, 2×9H, OCH$_2$CH$_3$), 1.55 and 1.60 (d, 2×2H, SiCH$_2$CH=CH), 1.61 and 1.62 (d, 2×3H, CH=CHCH$_3$), 3.81 and 3.82 (q, 2×6H, OCH$_2$CH$_3$), 5.38 to 5.48 (m, 4×1H, CH=CH). $^{13}$C {$^1$H} NMR (CDCl$_3$): δ=11.84 (SiCH$_2$CH=CH); 18.20 and 18.23 (CH=CHCH$_3$); 18.36 and 18.38 (OCH$_2$CH$_3$); 58.64 and 58.65 (OCH$_2$CH$_3$); 123.33, 123.68, 124.46, 125.31 (CH=CH).

Example 9

Silylation of TBE with MD$^H$M Using ($^{Mes}$PDI)CoCH$_3$

This reaction was carried out in a manner similar to the silylation of 1-butene using 0.100 g (0.449 mmol) of MD$^H$M, 0.004 g (0.009 mmol) of ($^{Mes}$PDI)CoCH$_3$ and 0.891 mmol of TBE. Analysis of the volatiles by $^1$H NMR spectroscopy showed a 4:1 mixture of unreacted TBE and 2,2-dimethylbutane (33% conversion). Analysis of the silane product by GC and NMR spectroscopy showed only trans-1-bis(trimethylsiloxy)methylsilyl-3,3-dimethyl-1-butene.
$^1$H NMR (CDCl$_3$): δ=0.00 (s, 3H, (OTMS)$_2$SiCH$_3$), 0.09 (s, 18H, OSi(CH$_3$)$_3$), 0.99 (s, 9H, C(CH$_3$)$_3$), 5.37 (d, J=19.07, 1H SiCH=CH), 6.13 (d, J=19.07 Hz, 1H, CH=CHC(CH$_3$)$_3$). $^{13}$C {$^1$H} NMR (CDCl$_3$): δ=0.00 ((OTMS)$_2$SiCH$_3$); 2.01 (OSi(CH$_3$)$_3$); 28.96 (C(CH$_3$)$_3$); 34.91 (C(CH$_3$)$_3$); 121.01 (SiCH=CH); 159.23 (SiCH=CH).

Example 10

Silylation of N,N-Dimethylallylamine with Different Silanes Using ($^{Mes}$PDI)CoCH$_3$ and ($^{Mes}$PDI)CoN$_2$ In a nitrogen-filled drybox, a scintillation vial was charged with 0.090 g (1.1 mmol) of N,N-dimethylallylamine and 0.5 mmol (0.5 equiv) of the silane (0.118 g MD$^H$M, 0.087 g (EtO)$_3$SiH or 0.062 g Et$_3$SiH). 0.01 mmol (1 mol %) of the cobalt complex [0.005 g ($^{Mes}$PDI)CoCH$_3$ or 0.005 g ($^{Mes}$PDI)CoN$_2$] was then added and the reaction was stirred for one hour at room temperature. The reaction was quenched by exposure to air and the product mixture was analyzed by NMR spectroscopy. Results are shown in Table 5.

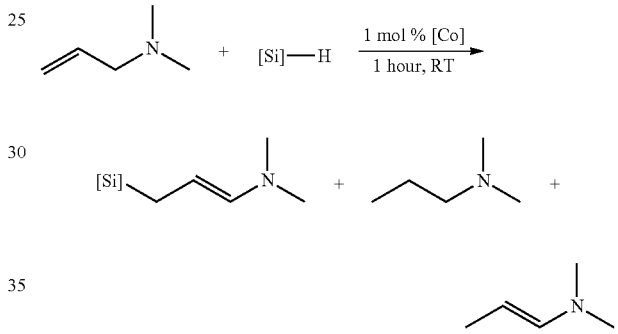

TABLE 5

| | | | Silylation of N,N-dimethylallylamine with various silanes.* | | |
|---|---|---|---|---|---|
| Catalyst | Silane | % conv | [Si]⌒⌒N⌒ | ⌒⌒N⌒ | ⌒⌒N⌒ |
| (structure shown) | MD$^H$M | >95 | 53 | 42 | Trace |
| | (EtO)$_3$SiH | >95 | 47 | 47 | Trace |
| | Et$_3$SiH | <5 | — | — | — |

TABLE 5-continued

Silylation of N,N-dimethylallylamine with various silanes.*

| Catalyst | Silane | % conv | [Si]∼∼∼N | ∼∼∼N | ∼∼∼N |
|---|---|---|---|---|---|
| (structure shown) | MD$^H$M | >95 | 38 | 28 | 29 |
| | (EtO)$_3$SiH | >95 | 45 | 50 | Trace |
| | Et$_3$SiH | 65 | — | — | 65 |

*% Conversion and product distribution determined by $^1$H NMR spectroscopy.

Characterization of Products

N,N-dimethyl-3-bis(trimethylsiloxy)methylsilyl-1-propenylamine $^1$H NMR (benzene-d$_6$): δ=0.14 (s, 3H, (OTMS)$_2$SiCH$_3$), 0.18 (s, 18H, OSi(CH$_3$)$_3$), 1.50 (dd, J=7.7, 1.2 Hz, 2H, SiCH$_2$CH=CH), 2.35 (s, 6H, N(CH$_3$)$_2$), 4.25 (dt, J=13.6, 7.7 Hz, 1H, CH$_2$CH=CH), 5.80 (dt, J=13.6, 1.2 Hz, 1H, CH$_2$CH=CH). $^{13}$C {$^1$H} NMR (benzene-d$_6$): δ=0.61 ((OTMS)$_2$SiCH$_3$), 2.12 (OSi(CH$_3$)$_3$), 20.49 (SiCH$_2$CH=CH), 41.08 (N(CH$_3$)$_2$), 94.09 (CH$_2$CH=CH), 140.57 (CH$_2$CH=CH).

N,N-dimethyl-3-triethoxysilyl-1-propenylamine $^1$H NMR (benzene-d$_6$): δ=1.18 (t, J=7.0, 9H, OCH$_2$CH$_3$), 1.66 (dd, J=7.5, 1.2 Hz, 2H, SiCH$_2$CH=CH), 2.30 (s, 6H, N(CH$_3$)$_2$), 3.84 (q, J=7.0, 6H, OCH$_2$CH$_3$), 4.31 (dt, J=13.6, 7.5 Hz, 1H, CH$_2$CH=CH), 5.85 (dt, J=13.6, 1.2 Hz, 1H, CH$_2$CH=CH). $^{13}$C {$^1$H} NMR (benzene-d$_6$): δ=13.48 (SiCH$_2$CH=CH), 18.41 (OCH$_2$CH$_3$), 40.98 (N(CH$_3$)$_2$), 58.65 (OCH$_2$CH$_3$), 92.95 (CH$_2$CH=CH), 140.82 (CH$_2$CH=CH).

Example 11

Silylation of Methyl Capped Allyl Polyether (H$_2$C=CHCH$_2$O(C$_2$H$_4$O)$_{8.9}$CH$_3$) with Methylbis(trimethylsilyloxy)silane (MD$^H$M)

A scintillation vial was charged with 0.100 g of methyl capped allyl polyether having an average formula of H$_2$C=CHCH$_2$O(C$_2$H$_4$O)$_{8.9}$CH$_3$ (0.215 mmol) and 0.025 g (0.11 mmol, 0.5 equiv) of MD$^H$M. To the stirring solution of polyether and silane was added 1 mg (0.002 mmol; 1 mol %) of ($^{Mes}$PDI)CoCH$_3$. The scintillation vial was sealed and removed from the drybox and placed in a 65° C. oil bath. The reaction mixture was stirred for 1 hour after which the vial was removed from the oil bath and the reaction was quenched by opening the vessel to air. Analysis of $^1$H NMR spectrum of the product established a 1:1 mixture of silylated product and propylpolyether.

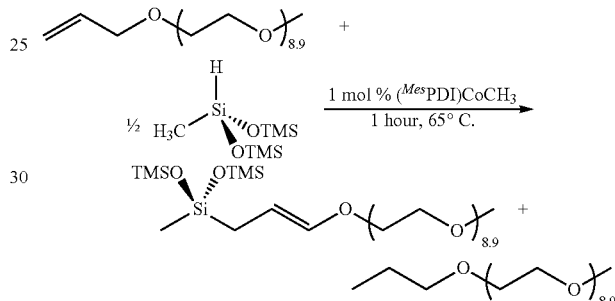

(OTMS)$_2$Si(CH$_3$)CH$_2$CH=CHO(C$_2$H$_4$O)$_{8.9}$CH$_3$ $^1$H NMR (CDCl$_3$): δ=−0.06 (s, 3H, (OTMS)$_2$SiCH$_3$), 0.03 (s, 18H, OSi(CH$_3$)$_3$), 1.55 (dd, J=7.8, 1.1 Hz, 2H, SiCH$_2$CH=CH), 3.32 (s, 3H, OCH$_3$), 3.5-3.7 (O—CH$_2$CH$_2$—O), 5.28 (dt, J=18.5, 1.1 Hz, 1H, CH$_2$CH=CH), 6.07 (dt, J=18.5, 7.8 Hz, 1H, CH$_2$CH=CH). $^{13}$C {$^1$H} NMR (CDCl$_3$): δ=0.11 ((OTMS)$_2$SiCH$_3$), 1.65 (OSi(CH$_3$)$_3$), 29.24 (SiCH$_2$CH=CH), 59.00 (OCH$_3$), 70-72 (O—CH$_2$CH$_2$—O), 127.02 (CH$_2$CH=CH), 144.38 (CH$_2$CH=CH).

Example 12

Crosslinking of M$^{vi}$D$_{120}$M$^{vi}$ (SL 6100) and MD$_{15}$D$^H_{30}$M (SL 6020) at Room Temperature A scintillation vial was charged with 1.0 g of M$^{vi}$D$_{120}$M$^{vi}$ (SL 6100) in which M$^{vi}$ is vinyl dimethyl SiO, and 0.044 g of MD$_{15}$D$^H_{30}$M (SL 6020). In a second vial, a solution of the catalyst was prepared by dissolving 0.010 g of ($^{Mes}$PDI)CoCH$_3$ or ($^{Mes}$PDI)CoN$_2$ in approximately 0.300 g of toluene. The catalyst solution was added to a stirring solution of SL 6100 and SL 6020 and the reaction was monitored for gel formation. The resulting gel after quenching the reaction by exposure to air was softer than that obtained from the same reaction using Karstedt's compound as catalyst.

Polymer crosslinking under neat conditions was also investigated by adding 0.010 g of ($^{Mes}$PDI)CoCH$_3$ or ($^{Mes}$P-

DI)CoN$_2$ to a stirring solution of 1.0 g SL 6100 and 0.044 g SL 6020. Soft gels were also obtained from these reactions.

Example 13

Crosslinking of M$^{vi}$D$_{120}$M$^{vi}$ (SL 6100) and MD$_{15}$D$^H_{30}$M (SL 6020) at 65° C.

These reactions were carried out in a manner similar to those performed at room temperature, with the additional steps of sealing the scintillation vials, removing them from the drybox and placing them in a 65° C. oil bath. The resulting gels after quenching the reaction were indistinguishable from that obtained from the same reaction using Karstedt's compound as catalyst. Results are shown in Table 6.

TABLE 6

Gelation time for the crosslinking of SL 6100 and SL 6020 under various reaction conditions.

| Catalyst | Reaction Condtions | Gelation time | Quality of Gel | Color |
|---|---|---|---|---|
| 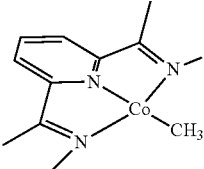 | RT, in toluene | 5 min | soft | dark yellow |
| | RT, neat | 60 min | soft | light gray |
| | 65° C., toluene | 5 min | hard | yellow |
| | 65° C., neat | 15 min | hard | light yellow |
| 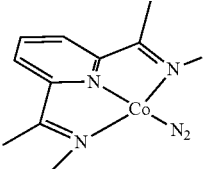 | RT, in toluene | 20 min | soft | dark yellow |
| | RT, neat | 60 min | soft | light gray |
| | 65° C., toluene | 5 min | hard | yellow |
| | 65° C., neat | 15 min | hard | light yellow |

Double Silylation Experiments

Example 14

Silylation of 1-bis(trimethylsiloxy)methylsilyl-2-octene with MD$^H$M Using ($^{Mes}$PDI)CoCH$_3$ This experiment was performed in a manner similar to the silylation of 1-octene using 0.100 g (0.301 mmol) of 1-bis(trimethylsiloxy)methylsilyl-2-octene, 0.034 g (0.152 mmol, 0.51 equiv) of MD$^H$M, and 0.001 g (0.002 mmol, 1 mol %) of ($^{Mes}$PDI)CoCH$_3$. The reaction was stirred at room temperature for 24 hours and quenched by exposure to air. Analysis of the mixture by GC-FID, GC-MS and NMR spectroscopy showed an approximately 1:1 mixture of 1-bis (trimethylsiloxy)methylsilyloctane and 1,8-bis(bis(trimethylsiloxy)methylsilyl)-2-octene (major isomer).

Attempts to silylate 1-triethoxysilyl-2-octene with MD$^H$M yielded a mixture of disilylated products concomitant with the formation of 1-triethoxysilyloctane. Silylation of 1-bis(trimethylsiloxy)methylsilyl-2-octene and 1-triethoxysilyl-2-octene with triethoxysilane under the same conditions yielded only the hydrogenated products, 1-bis (trimethylsiloxy)methylsilyloctane and 1-triethoxysilyloctane, respectively.

Example 15

Alternative Procedure for the Double Silylation of 1-Octene with MD$^H$M Using ($^{Mes}$PDI)CoCH$_3$ This experiment is performed in a manner similar to the silylation of 1-octene using 0.100 g (0.891 mmol) of 1-octene, 0.150 g (0.674 mmol, 0.756 equiv) of MD$^H$M and 0.004 g (0.008 mmol, 1 mol %) of ($^{Mes}$PDI)CoCH$_3$. The reaction was stirred at room temperature for 24 hours and quenched by exposure to air. Analysis of the mixture by GC-FID showed a 1:0.5:0.5 mixture of octane, 1-bis(trimethylsiloxy)methylsilyloctane and 1,8-bis(bis(trimethylsiloxy)methylsilyl)-2-octene (major isomer), respectively.

Example 16

Silylation of 1-Bis(Trimethylsiloxy)Methylsilyl-2-Butene with MD$^H$M Using ($^{Mes}$PDI)CoCH$_3$ This experiment was performed in a manner similar to the silylation of 1-bis(trimethylsiloxy)methylsilyl-2-octene using 0.100 g (0.361 mmol) of 1-bis(trimethylsiloxy)methylsilyl-2-butene, 0.040 g (0.18 mmol, 0.50 equiv) of MD$^H$M and 0.002 g (0.004 mmol, 1 mol %) of ($^{Mes}$PDI)CoCH$_3$. The reaction was stirred for 24 hours and quenched by exposure to air. Analysis of the mixture by NMR spectroscopy showed the following product distribution: 50% 1-bis(trimethylsiloxy)methylsilylbutane; 26% trans-1,4-bis(bis(trimethylsiloxy)-methylsilyl)-2-butene; 17% cis-1,4-bis(bis(trimethylsiloxy)methylsilyl)-2-butene; 5% trans-1,3-bis(bis(trimethylsiloxy)methylsilyl)-1-butene; and, 2% trans-1,4-bis(bis(trimethylsiloxy)methylsilyl)-1-butene.

Characterization of Products 1-bis(trimethylsiloxy)methylsilylbutane $^1$H NMR (CDCl$_3$): δ=0.01 (s, 3H, (OTMS)$_2$SiCH$_3$), 0.09 (s, 18H, OSi(CH$_3$)$_3$), 0.45 (m, 2H, SiCH$_2$CH$_2$CH$_2$CH$_3$), 0.88 (t, 3H, SiCH$_2$CH$_2$CH$_2$CH$_3$), 1.26-1.33 (m, 4H, SiCH$_2$CH$_2$CH$_2$CH$_3$). $^{13}$C {$^1$H} NMR (CDCl$_3$): δ=−0.66 ((OTMS)$_2$SiCH$_3$), 2.02 (OSi(CH$_3$)$_3$), 13.98 (SiCH$_2$CH$_2$CH$_2$CH$_3$), 17.46 (SiCH$_2$CH$_2$CH$_2$CH$_3$), 25.35 and 26.36 (SiCH$_2$CH$_2$CH$_2$CH$_3$).

Trans-1,4-bis(bis(trimethylsiloxy)methylsilyl)-2-butene $^1$H NMR (CDCl$_3$): δ=0.01 (s, 3H, (OTMS)$_2$SiCH$_3$), 0.09 (s, 18H, OSi(CH$_3$)$_3$), 1.39 (d, 4H, SiCH$_2$CH=CHCH$_2$Si), 5.21 (t, 2H, SiCH$_2$CH=CHCH$_2$Si). $^{13}$C {$^1$H} NMR (CDCl$_3$): δ=−0.66 ((OTMS)$_2$SiCH$_3$), 2.02 (OSi(CH$_3$)$_3$), 23.95 (SiCH$_2$CH=CHCH$_2$Si), 124.28 (SiCH$_2$CH=CHCH$_2$Si).

Cis-1,4-bis(bis(trimethylsiloxy)methylsilyl)-2-butene $^1$H NMR (CDCl$_3$): δ=0.01 (s, 3H, (OTMS)$_2$SiCH$_3$), 0.09 (s, 18H, OSi(CH$_3$)$_3$), 1.41 (d, 4H, SiCH$_2$CH=CHCH$_2$Si), 5.31 (t, 2H, SiCH$_2$CH=CHCH$_2$Si). $^{13}$C {$^1$H} NMR (CDCl$_3$): δ=−0.38 ((OTMS)$_2$SiCH$_3$), 2.01 (OSi(CH$_3$)$_3$), 19.12 (SiCH$_2$CH=CHCH$_2$Si), 122.86 (SiCH$_2$CH=CHCH$_2$Si).

Trans-1,3-bis(bis(trimethylsiloxy)methylsilyl)-1-butene $^1$H NMR (CDCl$_3$): δ=0.01 (s, 3H, (OTMS)$_2$SiCH$_3$), 0.09 (s, 18H, OSi(CH$_3$)$_3$), 1.04 (d, 3H, CHCH$_3$), 1.64 (m, 1H, CHCH$_3$), 5.28 (d, 1H, SiCH=CH), 6.27 (dd, 1H, SiCH=CH). $^{13}$C {$^1$H} NMR (CDCl$_3$): δ=−0.13 ((OTMS)$_2$SiCH$_3$), 2.00 (OSi(CH$_3$)$_3$), 12.07 (CHCH$_3$), 31.69 (CHCH$_3$), 123.37 (SiCH=CH), 151.01 (SiCH=CH).

Trans-1,4-bis(bis(trimethylsiloxy)methylsilyl)-1-butene $^1$H NMR (CDCl$_3$): δ=0.01 (s, 3H, (OTMS)$_2$SiCH$_3$), 0.09 (s, 18H, OSi(CH$_3$)$_3$), 0.58 (m, 2H, CH$_2$CH$_2$Si), 2.11 (m, 2H, CH$_2$CH$_2$Si), 5.46 (d, 1H, SiCH=CH), 6.20 (m, 1H, SiCH=CH). $^{13}$C {$^1$H} NMR (CDCl$_3$): δ=0.29 ((OTMS)$_2$SiCH$_3$), 2.07 (OSi(CH$_3$)$_3$), 16.28 (CH$_2$CH$_2$Si), 29.79 (CH$_2$CH$_2$Si), 125.73 (SiCH=CH), 151.52 (SiCH=CH).

Example 17A-17F

Crosslinking of Polysiloxanes with Olefins Using ($^{Mes}$PDI)CoCH$_3$

A 20 mL scintillation vial was charged with 0.002 g (0.004 mmol, 2000 ppm catalyst loading) of ($^{Mes}$PDI)CoCH$_3$ and the olefin (see Table 7 for specific amounts). The mixture was stirred until a homogenous pink solution was obtained. This step typically required between 5 and 20 minutes of stirring. The polysiloxane (1:0.75 ratio of C=C to Si—H, Table 7) was then added to the reaction vessel and the mixture was stirred in an oil bath at 65° C. for 4-6 hours. The resulting gel was crushed into a powder using a mortar and pestle, washed with hexanes to remove the alkane by-product, and dried in vacuo overnight.

Each of the hexane-extracted samples was analyzed by nuclear magnetic resonance (NMR) spectroscopy on a Bruker AVANCE 400WB Spectrometer operating at field strength of 9.40 T; $^1$H's resonate at 400 MHz. Single pulse excitation (SPE) pulse sequence with magic angle spinning (MAS) was used with a delay of 150 seconds for the {$^1$H-$^{13}$C} SPE/MAS NMR spectra or a delay of 300 seconds for the {$^1$H-$^{29}$Si} SPE/MAS NMR spectra. Cross-polarization (CP) pulse sequence with magic angle spinning (MAS) was used with a delay of 10 seconds and a contact time of 5 ms for the {$^1$H-$^{13}$C} CP/MAS NMR spectra. About 0.1 g of each sample was packed into a 4 mm zirconia (ZrO$_2$) rotor with a Kel-F cap and the rotor spun at ~8 to 10.8 kHz for the $^{29}$Si data and ~10.8 kHz for the $^{13}$C data. The number of co-added scans were 1000 ($^{13}$C) or 512 ($^{29}$Si) for the SPE data and 16,000 for the CP/MAS $^{13}$C data. The processing parameters used were zero-filling to 4× and LB of 5 or 15 Hz for the $^{13}$C data or 30 Hz for the $^{29}$Si data.

TABLE 7

Crosslinking of polysiloxanes with olefins using ($^{Mes}$PDI)CoCH$_3$.

| EXAMPLE | Polysiloxane | Olefin | Polymer Yield |
|---|---|---|---|
| 17A | MD$_{15}$D$^H_{30}$M (0.500 g) | 1-Octene (0.750 g) | 0.680 g |
| 17B | MD$_{15}$D$^H_{30}$M (0.285 g) | 1-Octadecene (0.965 g) | 0.733 g |
| 17C | MD$_{13}$D$^H_{5.5}$M (0.825 g) | 1-Octene (0.425 g) | 0.905 g |
| 17D | MD$_{13}$D$^H_{5.5}$M (0.580 g) | 1-Octadecene (0.672 g) | 0.865 g |
| 17E | MD$_{13}$D$^H_{5.5}$M (0.665 g) and M$^H$D$_{45}$M$^H$ (0.225 g) | 1-Octene (0.360 g) | 0.894 g |
| 17F | MD$_{13}$D$^H_{5.5}$M (0.490 g) and M$^H$D$_{45}$M$^H$ (0.165 g) | 1-Octadecene (0.595 g) | 0.789 g |

$^{13}$C NMR Results

1. Olefin: 1-Octene

The chemical shifts and their assignments of the $^{13}$C SPE/MAS and CP/MAS NMR spectra of samples from Examples 18A, 18C, and 18E are summarized in Table 8. The spectra show a multiple of signals observed in three distinct chemical shift regions, δ 2 to δ −2 consistent with methyl on silicon (CH$_3$Si), δ 14 to δ 35 consistent with linear type hydrocarbons and δ 124 to δ 135 due to olefinic (sp$^2$) carbons. No peak was observed at ~δ 115 indicating no residual unreacted 1-octene. A comparison of the data from the two different experiments shows significant differences. There is a significant loss in area for the CH$_2$, CH$_3$, and olefinic carbons. The results are consistent with the more mobile phase in the sample being saturated and unsaturated hydrocarbons, while the more rigid phase would consist of the following type structure, =SiCH$_2$CH$_2$CH$_2$(CH$_2$)$_2$CH$_2$CH$_2$CH$_3$Si. However, in the CP experiment there is still a large amount of olefinic signals. This result suggests the presence of unsaturated structures with internal double bonds (note that the double bond can be in positions 2 thru 6), =SiCH$_2$CH$_2$CH=CH(CH$_2$)$_2$CH$_2$CH$_2$CH$_3$.

The two signals observed at δ 125 and δ 131 due to the olefinic carbons are found with approximate equal intensity. The signals are consistent with the double bond being in position 2 or 6. The CP data for sample 18A show a very weak peak observed at δ 14 indicating that if the double bond is in position 6 the major configuration must be trans. The methyl group in the trans 6-position, —CH=CHCH$_3$, would overlap the signal observed at δ 18. The weaker signals observed around δ 130 are consistent with the double bond being in position 3, 4, or 5.

TABLE 8

$^{13}C$ SPE/MAS & CP/MAS NMR Intensity Data for 1-Octene Samples (Examples 17A, 17C, 17E)

| Chemical Shift (δ, ppm) | Assignment | Example 17A SPE | Example 17A CP | Example 17C SPE | Example 17C CP | Example 17E SPE | Example 17E CP |
|---|---|---|---|---|---|---|---|
| 133 to 125 | sp$^2$ carbons: double bond | 6.35 | 3.19 | 4.70 | 2.06 | 3.89 | 1.88 |
| 109.3 | | | | 1.07 | | 1.83 | |
| 40 to 20* | —CH$_2$— groups | 15.06 | 6.99 | 10.22 | 5.94 | 10.52 | 5.96 |
| 36.9 | | 2.44 | trace | | 0.29 | | |
| 33.6 | Si—CH$_2$CH$_2$CH$_2$— & —CH$_2$CH$_2$CH$_3$ (#3 & #6) | 2.87 | 2.47 | | 1.91 | | |
| 30.3 | 4$^{th}$ —CH$_2$— from either end | 3.33 | 1.09 | | 1.16 | | |
| 27.8 | | 0.96 | 0.31 | | 0.27 | — | trace |
| 23.7 | Si—CH$_2$CH$_2$— & —CH$_2$CH$_3$ (#2 & #7) | 5.17 | 2.73 | | 2.31 | | |
| 18.1 | SiCH$_2$— (#1) | 2.00 | 2.00 | 2.00 | 2.00 | 2.00 | 2.00 |
| 14.8 | CH$_3$— (#8) | 2.98 | 0.22 | 1.38 | — | 1.41 | — |
| 2 to –3 | SiCH$_3$ | 9.98 | 5.28 | 20.62 | 6.33 | 2963 | 6.39 |

*The areas of all the methylene carbons are grouped together.

2. Olefin: 1-Octadecene

The chemical shifts and their assignments of the $^{13}$C SPE/MAS and CP/MAS NMR spectra of samples from Examples 18B, 18D and 18F are summarized in Table 9. The spectra are very similar those of the 1-octene crosslinked samples in that they show a multiple of signals in three distinct chemical shift regions, δ 2 to δ –2 consistent with methyl on silicon (CH$_3$Si), δ 14 to δ 35 consistent with linear type hydrocarbons and δ 124 to δ 135 due to olefinic (sp$^2$) carbons. However, the signal observed at ~δ 30 is significantly stronger due to the higher number of methylene groups (CH$_2$) in the 1-octadecene starting material. A second difference is observed in the olefinic chemical shift range. The peak observed at ~δ 125 is not observed with the same intensity as the peak at ~δ 131. This result would suggest the double bond is not near one of the ends but is internal.

The following list summarizes the similarities to the results of the 1-octene data.

No peak is observed at ~δ 115 indicating no residual unreacted 1-octadecene.

The SPE and CP data show significant loss in peak area for the CH$_2$, CH$_3$, and olefinic carbons.

The more mobile phase in the sample being saturated and unsaturated hydrocarbons, while the more rigid phase would consist of the following type structure, ≡SiCH$_2$CH$_2$CH$_2$(CH$_2$)$_{12}$CH$_2$CH$_2$CH$_2$Si≡.

The CP experiment shows a large amount of olefinic signals indicating the following type structure may be present (note that the double bond could be in positions 2 thru 16), ≡SiCH$_2$CH$_2$CH=CH(CH$_2$)$_{12}$CH$_2$CH$_2$CH$_3$. The loss in area of the CH$_3$ peak observed at δ 15 in the CP/MAS experiment could be due to the combination of the methyl group being associated to a hydrocarbon type molecule in the mobile phase and from the following type structure; ≡SiCH$_2$CH=CHCH$_2$(CH$_2$)$_{13}$CH$_3$, and the lost intensity is due to the group being at the end of the molecule resulting in greater mobility. The methyl group is farther from the point of cross-linking

TABLE 9

$^{13}C$ SPE/MAS & CP/MAS NMR Intensity Data of 1-Octadecene Samples (Examples 17B, 17D and 17F)

| Chemical Shift (δ, ppm) | Tentative Assignment | Example 17B SPE | Example 17B CP | Example 17D SPE | Example 17D CP | Example 17F SPE | Example 17F CP |
|---|---|---|---|---|---|---|---|
| 133 to 125 | sp$^2$ carbons: double bond | 3.47 | 1.73 | 3.69 | 2.01 | | |
| 109.3 | | | | 1.96 | | | |
| 40 to 20* | —CH$_2$— groups | 37.67 | 13.25 | 30.89 | 17.46 | | |
| 36.9 | | — | — | — | — | | |
| 33.6 | Si—CH$_2$CH$_2$CH$_2$— & —CH$_2$CH$_2$CH$_3$ (#3 & #6) | | 2.58 | | | | |
| 30.3 | 4$^{th}$ —CH$_2$— from either end | | 8.33 | | | | |
| 27.8 | | trace | trace | trace | trace | | |
| 23.7 | Si—CH$_2$CH$_2$— & —CH$_2$CH$_3$ (#2 & #7) | 5.28 | 2.34 | | | | |
| 18.1 | SiCH$_2$— (#1) | 2.00 | 2.00 | 2.00 | 2.00 | | |

TABLE 9-continued $^{13}$C SPE/MAS & CP/MAS NMR Intensity Data of 1-Octadecene Samples
(Examples 17B, 17D and 17F)

| Chemical Shift (δ, ppm) | Tentative Assignment | Example 17B SPE | Example 17B CP | Example 17D SPE | Example 17D CP | Example 17F SPE | Example 17F CP |
|---|---|---|---|---|---|---|---|
| 14.8 | $\underline{CH_3}$— (#8) | 2.60 | — | 1.70 | — | | |
| 2 to −3 | $\underline{SiCH_3}$ | 6.90 | 3.58 | 19.91 | 4.52 | | |

*The areas of all the methylene carbons are grouped together.

$^{29}$Si NMR Results

Chemical shifts and assignments of the $^{29}$Si SPE/MAS NMR spectra for the six samples of Example 18 are summarized in Table 10. The signal observed at δ −26 is assigned to a D* with the organofunctional group having the double bond in the allylic or 2 position, $\equiv SiCH_2CH=CHCH_2(CH_2)_xCH_3$. This signal is very strong in Example 17A compared to the spectra of the other samples. Also, there appears to be a slight trend in this peak being slightly larger when the samples are prepared with 1-octene than with 1-octadecene. The integral of this signal is grouped with the stronger signals observed at δ −22 because of the peak overlap for the majority of the samples.

The spectra of the two samples (Examples 17A and 17B) prepared with the SiH fluid, $MD_{15}D^H{}_{30}M$ show a large amount of what could be a combination of cyclic $D_3$ and $D^1$ type species and do not contain a signal at δ −35.

TABLE 10

$^{29}$Si SPE/MAS NMR Intensity Data for Example 17A-17F

| Chemical Shift (δ, ppm) | Assignment | Ex 17A | Ex 17B | Ex 17C | Ex 17D | Ex 17E | Ex 17F |
|---|---|---|---|---|---|---|---|
| 7 | M | 2.00 | 2.00 | 2.00 | 2.00 | 2.00 | 2.00 |
| −5 to −15 | Cyclic $D_3$ & $D^1$ | 8.05 | 10.28 | 0.97 | 0.96 | 0.87 | |
| −22 | D & D* | 39.18 | 42.28 | 22.36 | 23.45 | 25.41 | |
| −26 | D* | | | | | | |
| −35 | D' | — | — | 0.59 | 0.33 | 0.43 | |
| −37 | D' | 8.15 | 2.76 | | | | |
| −55 | $T^2$ | 0.85 | — | — | — | 0.10 | |
| −66 | $T^3$ | 0.76 | — | 0.22 | 0.22 | 0.18 | |

In terms of the rheological characteristics of the products, one would predict different moduli resulting from molecules dependent on the cross-linked densities and the chain lengths of the linking molecule.

Examples 18A-18B

These Examples illustrate deuterium labeling experiments that were done to establish that the occurrence of dehydrogenative hydrosilylation when the reaction of to hydridosiloxanes and olefins is catalyzed by ($^{Mes}$PDI)CoCH$_3$.

Example 18A

Silylation of 1-Octene with (OTMS)$_2$CH$_3$Si-D (MD$^H$M-d$_1$)

This reaction was performed in a manner similar to the silylation of 1-octene with MD$^H$M using 0.050 g (0.45 mmol) of 1-octene, 0.050 g (0.22 mmol, 0.5 equiv) of MD$^H$M-d$_1$ (70% deuterated), and 0.002 g (0.004 mmol, 1 mol %) of ($^{Mes}$PDI)CoCH$_3$. The reaction was quenched after stirring for one hour at room temperature. Analysis of the $^2$H NMR spectrum of the product mixture showed deuterium incorporation into both the methyl and methylene groups of octane as well as traces of deuterium on $C^b$, $C^c$, and $C^d$ of 1-bis(trimethylsiloxy)methylsilyl-2-octene.

Example 18B

Deuteration of
1-bis(trimethylsiloxy)methylsilyl-2-octene

In nitrogen-filled drybox, a J. Young tube was charged with 0.080 g (0.24 mmol) of 1-bis(trimethylsiloxy)methylsilyl-2-octene, 0.005 g (0.011 mmol, 4 mol %) of ($^{Mes}$PDI) CoCH$_3$, and approximately 0.7 mL of benzene-d$_6$. The tube was degassed and approximately 1 atm of D$_2$ was admitted. The solution was thawed to room temperature and then placed in an oil bath at 45° C. for 16 hours. Analysis of the $^1$H and $^2$H NMR spectra of the product mixture showed partial deuteration of the starting material to the fully saturated product with deuterium scrambled in all along the octyl chains both compounds. Deutertation occurred principally at the C2 and C3 positions, indicating that unsaturation in the starting material was principally allylic and not vinylic.

Examples 19A-19D

Olefin Isomerization Experiments

Example 19A shows that ($^{Mes}$PDI)CoCH$_3$ does not isomerize 1-octene.

A scintillation vial was charged with 0.100 g (0.891 mmol) of 1-octene and 0.004 g (0.008 mmol, 1 mol %) of ($^{Mes}$PDI)CoCH$_3$. The solution was stirred for one hour at room temperature and then quenched by exposure to air. The $^1$H NMR spectrum of the product showed only 1-octene and traces of free ligand and no evidence for olefin isomerization.

Example 19B shows that 1-octene isomerization was not observed with ($^{Mes}$PDI)CoCH$_3$ and trace amounts of hydridotrisiloxane, MD$^H$M.

This experiment was performed in the same manner as the experiment described above (Example 21A) using 0.100 g (0.891 mmol) of 1-octene, 0.004 g (0.008 mmol, 1 mol %) of ($^{Mes}$PDI)CoCH$_3$, and 0.014 g (0.063 mmol, 7 mol %) of MD$^H$M. The $^1$H NMR spectrum of the product showed only 1-octene, traces of free ligand and 1-bis(trimethylsiloxy) methylsilyl-2-octene, and no evidence for olefin isomerization.

Example 19C illustrates isomerization of N,N-dimethylallylylamine, (CH$_3$)$_2$NCH$_2$CH=CH$_2$, using ($^{Mes}$PDI)CoCH$_3$.

A J. Young tube was charged with 0.017 g (0.20 mmol) of N,N-dimethylallylamine, 0.002 g (0.004 mmol, 2 mol %) of ($^{Mes}$PDI)CoCH$_3$ and approximately 0.7 mL of benzene-d$_6$. The solution was allowed sit at room temperature and monitored using $^1$H NMR spectroscopy. Isomerization of the starting material to N,N-dimethyl-1-propenylamine, (CH$_3$)$_2$NCH=CHCH$_3$, was 20% complete after 8 hours and 65% after 46 hours.

Example 19D illustrates isomerization of N,N-dimethylallylamine, (CH$_3$)$_2$NCH$_2$CH=CH$_2$, using ($^{Mes}$PDI)CoCH$_3$ and trace amounts of the hydrido trisiloxane, MD$^H$M.

This reaction was carried out in a manner similar to the experiment described above (Example 19C) using 0.091 g (1.1 mmol) of N,N-dimethylallylamine, 0.003 g (0.006 mmol, 0.6 mol %) of ($^{Mes}$PDI)CoCH$_3$ and 0.006 g (0.03 mmol, 3 mol %) of MD$^H$M. Isomerization of the starting material to N,N-dimethyl-1-propenylamine, (CH$_3$)$_2$NCH=CHCH$_3$ was 90% complete after 8 hours and >95% after 24 hours.

Example 20A-20C

Silylation of Propylene with Different Silanes Using ($^{Mes}$PDI)CoCH$_3$

This reaction was carried out in a manner similar to the silylation of 1-butene using 0.11 mmol of silane (0.025 g of MD$^H$M, 0.018 g of (EtO)$_3$SiH or 0.015 g of (OEt)$_2$CH$_3$SiH) 0.001 g (0.002 mmol) of ($^{Mes}$PDI)CoCH$_3$ and 5.6 mmol (50 equiv) of propylene. The non-volatiles were analyzed by NMR spectroscopy.

TABLE 11

Product Distribution for the Silylation of Propylene.

| Silane | [Si]-allyl | [Si]-propyl | Disproportionation Product |
|---|---|---|---|
| Ex 20A: MD$^H$M | 82% | 28% | None |
| Ex 20B: (EtO)$_3$SiH | 40% | 20% | 40% |
| Ex 20C: Me(OEt)$_2$SiH | 60% | 30% | 10% |

Characterization of Products of Example 20A 3-bis(trimethylsiloxy)methylsilyl-1-propene $^1$H NMR (CDCl$_3$): δ=0.03 (s, 3H, (OTMS)$_2$SiCH$_3$), 0.09 (s, 18H, OSi(CH$_3$)$_3$), 1.49 (d, J=8.1 Hz, 2H, SiCH$_2$CH=CH), 4.86 (d, J=6.3 Hz, 1H, CH$_2$CH=C(H)H), 4.88 (d, J=15 Hz, 1H, CH$_2$CH=C(H)H), 5.77 (m, 1H, CH$_2$CH=CH$_2$). $^{13}$C {$^1$H} NMR (CDCl$_3$): δ=−0.77 ((OTMS)$_2$SiCH$_3$), 1.97 (OSi(CH$_3$)$_3$), 25.82 (SiCH$_2$CH=CH), 113.72 (CH$_2$CH=CH$_2$), 134.28 (CH$_2$CH=CH$_2$).

1-bis(trimethylsiloxy)methylsilylpropane $^1$H NMR (CDCl$_3$): δ=0.00 (s, 3H, (OTMS)$_2$SiCH$_3$), 0.09 (s, 18H, OSi(CH$_3$)$_3$), 0.46 (m, 2H, SiCH$_2$CH$_2$CH$_3$), 0.95 (t, 3H, SiCH$_2$CH$_2$CH$_3$), 1.36 (m, 2H, SiCH$_2$CH$_2$CH$_3$). $^{13}$C {$^1$H} NMR (CDCl$_3$): δ=−0.07 ((OTMS)$_2$SiCH$_3$), 1.97 (OSi(CH$_3$)$_3$), 16.75 (SiCH$_2$CH$_2$CH$_3$), 18.05 (SiCH$_2$CH$_2$CH$_3$), 20.37 (SiCH$_2$CH$_2$CH$_3$).

Characterization of Products of Example 20B 3-triethoxysilyl-1-propene $^1$H NMR (CDCl$_3$): δ=1.22 (t, 9H, OCH$_2$CH$_3$), 1.67 (d, 2H, SiCH$_2$CH=CH), 3.84 (q, 6H, OCH$_2$CH$_3$), 4.90-5.05 (d, 2H, CH$_2$CH=CH$_2$), 5.81 (m, 1H, CH$_2$CH=CH$_2$). $^{13}$C {$^1$H} NMR (CDCl$_3$): δ=18.36 (OCH$_2$CH$_3$), 19.34 (SiCH$_2$CH=CH), 58.73 (OCH$_2$CH$_3$), 114.85 (CH$_2$CH=CH$_2$), 132.80 (CH$_2$CH=CH$_2$).

1-triethoxysilylpropane $^1$H NMR (CDCl$_3$): δ=0.63 (m, 2H, SiCH$_2$CH$_2$CH$_3$), 0.97 (t, 3H, SiCH$_2$CH$_2$CH$_3$), 1.22 (t, 9H, OCH$_2$CH$_3$), 1.45 (m, 2H, SiCH$_2$CH$_2$CH$_3$). $^{13}$C {$^1$H} NMR (CDCl$_3$): δ=10.94 (SiCH$_2$CH$_2$CH$_3$), 12.92 (SiCH$_2$CH$_2$CH$_3$), 16.50 (SiCH$_2$CH$_2$CH$_3$), 18.43 (OCH$_2$CH$_3$), 58.40 (OCH$_2$CH$_3$).

Characterization of Products of Example 20C 3-diethoxymethylsilyl-1-propene $^1$H NMR (CDCl$_3$): δ=0.11 (s, 3H, SiCH$_3$), 1.19 (t, 6H, OCH$_2$CH$_3$), 1.63 (d, 2H, SiCH$_2$CH=CH), 3.76 (q, 4H, OCH$_2$CH$_3$), 4.88 (d, 1H, CH$_2$CH=C(H)H), 4.93 (d, 1H, CH$_2$CH=C(H)H), 5.80 (m, 1H, CH$_2$CH=CH$_2$). $^{13}$C {$^1$H} NMR (CDCl$_3$): δ=−5.19 (SiCH$_3$), 18.44 (OCH$_2$CH$_3$), 21.92 (SiCH$_2$CH=CH), 58.41 (OCH$_2$CH$_3$), 114.45 (CH$_2$CH=CH$_2$), 133.36 (CH$_2$CH=CH$_2$).

1-diethoxymethylsilylpropane $^1$H NMR (CDCl$_3$): δ=0.08 (s, 3H, SiCH$_3$), 0.59 (m, 2H, SiCH$_2$CH$_2$CH$_3$), 0.94 (t, 3H, SiCH$_2$CH$_2$CH$_3$), 1.19 (t, 9H, OCH$_2$CH$_3$), 1.38 (m, 2H, SiCH$_2$CH$_2$CH$_3$). $^{13}$C {$^1$H} NMR (CDCl$_3$): δ=−4.76 (SiCH$_3$), 16.37 (SiCH$_2$CH$_2$CH$_3$), 16.53 (SiCH$_2$CH$_2$CH$_3$), 18.07 (SiCH$_2$CH$_2$CH$_3$), 18.50 (OCH$_2$CH$_3$), 58.13 (OCH$_2$CH$_3$).

Example 21

Tandem Catalysis Using ($^{Mes}$PDI)CoMe

A 20 mL scintillation vial was charged with 0.200 g (1.78 mmol) 1-octene and 0.200 g (0.899 mmol) MD$^H$M. 0.002 g (0.004 mmol, 0.5 mol %) of ($^{Mes}$PDI)CoMe was then added, and the reaction was stirred at room temperature for 15 minutes. Analysis of an aliquot of the reaction by GC established complete conversion to 1-(TMSO)$_2$MeSi-2-octene and octane. The reaction mixture was directly transferred to a thick-walled glass vessel, and the latter was degassed. One atm of H$_2$ was then admitted, and the reaction was stirred at room temperature for 16 hours. Analysis of the mixture by $^1$H NMR spectroscopy established 41% hydrogenation of the allylsilane to 1-(TMSO)$_2$MeSi-octane.

Example 22

Tandem Catalysis Using ($^{Mes}$PDI)CoMe

A 20 mL scintillation vial was charged with 0.112 g (1 mmol) 1-octene and 0.082 g (0.5 mmol) (EtO)$_3$SiH. 0.002 g (0.005 mmol, 1 mol %) of ($^{Mes}$PDI)CoMe was then added, and the reaction was stirred at room temperature for 1 h. Analysis of an aliquot of the reaction by GC established complete conversion to 1-triethoxysilyl-2-octene and octane. The reaction mixture was directly transferred to a thick-walled glass vessel, and the latter was degassed. One atm of H₂ was then admitted, and the reaction was stirred at room temperature for 16 hours. Analysis of the mixture by ¹H NMR spectroscopy established 32% hydrogenation of the allylsilane to 1-triethoxysilyloctane.

Example 23

Tandem Catalysis Using (^MesPDI)CoMe

A 20 mL scintillation vial was charged with 0.112 g (1 mmol) 1-octene and 0.058 g (0.5 mmol) Et₃SiH. 0.010 g (0.025 mmol, 5 mol %) of (^MesPDI)CoMe was then added, and the reaction was stirred at room temperature for 12 h. Analysis of an aliquot of the reaction by GC established complete conversion to 1-triethylsilyl-2-octene and octane. The reaction mixture was directly transferred to a thick-walled glass vessel, and the latter was degassed. One atm of H₂ was then admitted, and the reaction was stirred at room temperature for 16 hours. Analysis of the mixture by ¹H NMR spectroscopy established quantitative hydrogenation of the allylsilane to 1-triethylsilyl-octane.

Example 24

Reusability of the Initial Charge of (^MesPDI)CoMe for Catalysis

A 20 mL scintillation vial was charged with 0.100 g (0.891 mmol) of 1-octene and 0.100 (0.449 mmol) of MD^HM. 0.001 g (0.002 mmol) of (^MesPDI)CoMe was then added, and the reaction was stirred at room temperature. An aliquot of the reaction was analyzed by GC after 30 min, which established complete conversion of the substrates to the allylsilane product. The reaction vial containing the allylsilane product was then charged with another 0.100 g of 1-octene and 0.100 g of MD^HM. Complete conversion (based on GC analysis) of the second batch of substrates was observed after stirring the reaction for one hour at room temperature.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A process for producing a silylated product comprising:
(i) reacting a mixture comprising (a) an unsaturated compound containing at least one unsaturated functional group, (b) a silyl hydride containing at least one silylhydride functional group, and (c) a catalyst, optionally in the presence of a solvent, in order to produce a dehydrogenatively silylated product, wherein the catalyst is a complex of the Formula (I) or an adduct thereof;

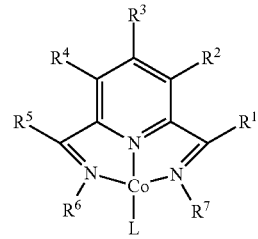

wherein
each occurrence of R¹, R², R³, R⁴, and R⁵ is independently hydrogen, C1-C18 alkyl, a C1-C18 substituted alkyl, an aryl, a substituted aryl, or an inert substituent, wherein one or more of R¹-R⁵, other than hydrogen, optionally contain at least one heteroatom; each occurrence of R⁶ and R⁷ is independently C1-C18 alkyl, C1-C18 substituted alkyl, aryl or substituted aryl, wherein R⁶ and R⁷ optionally contain at least one heteroatom; optionally any two of R¹-R⁷ vicinal to one another, R¹-R², and/or R⁴-R⁵ taken together may form a ring being a substituted or unsubstituted, saturated or unsaturated cyclic structure, with the proviso that R¹-R⁷ and R⁸-R⁶ are not taken to form a terpyridine ring; and
L is hydroxyl, or a C1-C18 alkyl, C1-C18 substituted alkyl, aryl, or substituted aryl group, wherein L optionally contains at least one heteroatom; and
(ii) using the catalyst complex to conduct subsequent reactions to produce additional dehydrogenatively silylated product and/or a saturated silylated product.

2. The process of claim 1 further comprising removing the complex and/or derivatives thereof from the dehydrogenative silylated product in operation (i).

3. The process of claim 2, wherein using the catalyst complex in operation (ii) comprises reacting, in a separate system, the complex and/or derivatives thereof removed from the dehydrogenative silylated product in operation (i) with an unsaturated compound containing at least one unsaturated functional group and a silyl hydride containing at least one silylhydride functional group.

4. The process of claim 1, wherein operation (ii) comprises adding additional unsaturated compound (a) and silyl hydride (b) to the system, and repeating reacting operation (i) in the presence of said catalyst (c) to produce additional dehydrogenatively silylated product.

5. The process of claim 1, wherein operation (ii) comprises reacting said dehydrogenatively silylated product in-situ with hydrogen in the presence of said catalyst (c) to produce a saturated and silylated product.

6. The process of claim 4 further comprising reacting said dehydrogenatively silylated product and/or said additional dehydrogenatively silylated product in-situ with hydrogen in the presence of said catalyst (c) to produce a saturated and silylated product.

7. The process of claim 1 wherein the dehydrogenatively silylated product comprises a silane or siloxane containing a silyl group and an unsaturated group.

8. The process of claim 3, wherein the unsaturated group is in the alpha or beta position relative to the silyl group.

9. The process of claim 1, wherein the molar ratio of the unsaturated group in said component (a) relative to the silylhydride functional group in said component (b) is less than equal to 1:1.

10. The process of claim 9, wherein the silane or siloxane of the dehydrogenatively silylated product contains one silyl group derived from component (b).

11. The process of claim 9, wherein the dehydrogenatively silylated product contains two or more terminal silyl groups derived from component (b).

12. The process of claim 9, wherein said process produces an α,ω-substituted alkane or alkene diol from a parent α,ω-bis(silyl) substituted alkane or alkene.

13. The process of claim 1, wherein the molar ratio of the unsaturated group in said component (a) relative to the silylhydride functional group in said component (b) is greater than 1:1.

14. The process of claim 13, wherein the silane or siloxane contains two or more silyl groups derived from component (b).

15. The process of claim 1, wherein said component (a) is a mono-unsaturated compound.

16. The process of claim 1, wherein said component (a) is selected from the group consisting of an olefin, a cycloalkene, an alkyl-capped allyl polyether, a vinyl-functional alkyl-capped allyl or methallyl polyether, an alkyl-capped terminally unsaturated amine, an alkyne, terminally unsaturated acrylate or methacrylate, unsaturated aryl ether, vinyl-functionalized polymer or oligomer, vinyl-functionalized silane, vinyl-functionalized silicone, unsaturated fatty acids, unsaturated esters, and combinations thereof.

17. The process of claim 12, wherein said component (a) is selected from the group consisting of N,N-dimethylallyl amine, allyloxy-substituted polyethers, cyclohexene, linear alpha olefins, internal olefins, branched olefins, unsaturated polyolefins, a vinyl siloxane of the Formula (VII), and combinations thereof, wherein Formula (VII) is

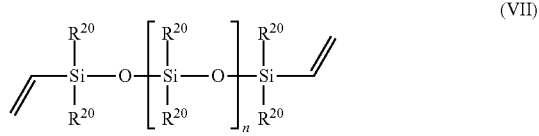

(VII)

wherein each occurrence of $R^{20}$ is independently a C1-C18 alkyl, C1-C18 substituted alkyl, C3-C18 terminal alkenyl, vinyl, aryl, or a substituted aryl, and n is greater than or equal to zero.

18. The process of claim 1, wherein said component (b) is selected from the group consisting of $R_aSiR_{4-a}$, $(RO)_aSiR_{4-a}$, $HSiR_a(OR)_{3-a}$, $R_3Si(CH_2)_f(SiR_2O)_kSiR_2H$, $(RO)_3Si(CH_2)_f(SiR_2O)_kSiR_2H$, $Q_uT_vT_p^H D_w D^H_x M^H_y M_z$, and combinations thereof, wherein Q is $SiO_{4/2}$, T is $R'SiO_{3/2}$, $T^H$ is $HSiO_{3/2}$, D is $R'_2SiO_{2/2}$, $D^H$ is $R'HSiO_{2/2}$, $M^H$ is $HR'_2SiO_{1/2}$, M is $R'_3SiO_{1/2}$, each occurrence of R and R' is independently C1-C18 alkyl, C1-C18 substituted alkyl, aryl, or substituted aryl, wherein R and R' optionally contain at least one heteroatom, each occurrence of a independently has a value from 1 to 3, f has a value of 1 to 8, k has a value of 1 to 11, p is from 0 to 20, u is from 0 to 20, v is from 0 to 20, w is from 0 to 1000, x is from 0 to 1000, y is from 0 to 20, and z is from 0 to 20, provided that p+x+y equals 1 to 3000, and the valences of the all the elements in the silyl hydride are satisfied.

19. The process of claim 14, wherein p, u, v, y, and z are from 0 to 10, w and x are from 0 to 100, wherein p+x+y equals 1 to 100.

20. The process of claim 1, wherein said component (b) has one of the following structures:

$R^{21}_a(R^{22}O)_bSiH$ (Formula VIII)

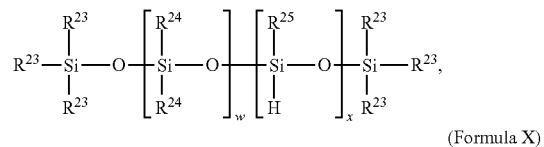

(Formula IX)

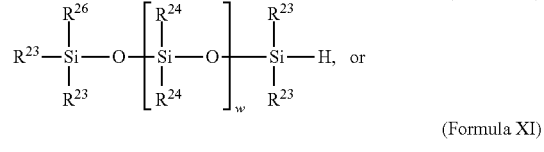

(Formula X)

(Formula XI)

wherein each occurrence of $R^{21}$, $R^{22}$, $R^{23}$, $R^{24}$, and $R^{25}$ is independently a C1-C18 alkyl, C1-C18 substituted alkyl, aryl, or substituted aryl, $R^{26}$ is hydrogen, a C1-C18 alkyl, C1-C18 substituted alkyl, aryl, or substituted aryl, x and w are independently greater than or equal to 0 (x is at least equal to 1 for Formula IX)), and a and b are integers from 0 to 3 provided that a+b=3.

21. The process of claim 1, wherein at least one of $R^6$ and $R^7$ is

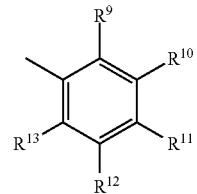

wherein each occurrence of $R^9$, $R^{10}$, $R^{11}$, $R^{12}$, and $R^{13}$ is independently hydrogen, C1-C18 alkyl, C1-C18 substituted alkyl, aryl, substituted aryl, or an inert substituent, wherein $R^9$-$R^{13}$, other than hydrogen, optionally contain at least one heteroatom.

22. The process of claim 21, wherein $R^9$ and $R^{13}$ are independently methyl, ethyl or isopropyl groups and $R^{11}$ is hydrogen or methyl.

23. The process of claim 22, wherein $R^9$, $R^{11}$, and $R^{13}$ are each methyl.

24. The process of claim 1, wherein $R^1$ and $R^5$ are independently methyl or phenyl groups.

25. The process of claim 1, wherein $R^2$, $R^3$ and $R^4$ are hydrogen.

26. The process of claim 1, wherein the complex is immobilized on a support.

27. The process of claim 26, wherein the support is selected from the group consisting of carbon, silica, alumina, $MgCl_2$, zirconia, polyethylene, polypropylene, polystyrene, poly(aminostyrene), sulfonated polystyrene, dendrimers, and combinations thereof.

28. The process of claim 26, wherein at least one of $R^1$ to $R^7$ contains a functional group that covalently bonds with the support.

29. The process of claim 1, wherein the catalyst is generated in-situ by contacting a catalyst precursor with an activator in the presence of a liquid medium containing at least one component selected from the group consisting of a solvent, the silyl hydride, the compound containing at least one unsaturated group, and combinations thereof, wherein the catalyst precursor is represented by structural Formula (III)

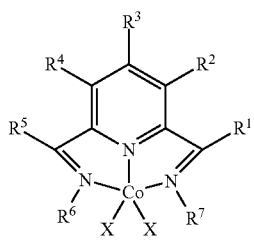

wherein
each occurrence of $R^1$, $R^2$, $R^3$, $R^4$, and $R^5$ is independently hydrogen, C1-C18 alkyl, a C1-C18 substituted alkyl, an aryl, a substituted aryl, or an inert substituent, wherein one or more of $R^1$-$R^5$, other than hydrogen, optionally contain at least one heteroatom; each occurrence of $R^6$ and $R^7$ is independently C1-C18 alkyl, C1-C18 substituted alkyl, aryl or substituted aryl, wherein $R^6$ and $R^7$ optionally contain at least one heteroatom; optionally any two of $R^1$-$R^7$ vicinal to one another, $R^1$-$R^2$, and/or $R^4$-$R^5$ taken together may form a ring being a substituted or unsubstituted, saturated or unsaturated cyclic structure, with the proviso that $R^1$-$R^7$ and $R^8$-$R^6$ are not taken to form a terpyridine ring; and
X is an anion selected from the group consisting of $F^-$, $Cl^-$, $Br^-$, $I^-$, $CF_3R^{14}SO_3^-$ or $R^{15}COO^-$, wherein $R^{14}$ is a covalent bond or a C1-C6 alkylene group, and $R^{15}$ is a substituted or unsubstituted C1-C10 hydrocarbyl group;
and wherein the activator is a reducing agent or an alkylating agent selected from the group consisting of $NaHBEt_3$, $CH_3Li$, DIBAL-H, LiHMDS, and combinations thereof.

30. The process of claim 1, wherein the reaction is conducted under an inert atmosphere.

31. The process of claim 1, wherein the reaction is conducted in the presence of a solvent selected from the group consisting of hydrocarbons, halogenated hydrocarbons, ethers, and combinations thereof.

32. The process of claim 1, wherein the reaction is carried out at a temperature of −40° C. to 200° C.

33. A composition produced from a process according to claim 1, wherein the composition contains the catalyst and/or derivatives thereof.

34. The composition of claim 33, comprising at least one component selected from the group consisting of silanes, silicone fluids, crosslinked silicones, or a combination of two or more thereof.

35. A process for producing a crosslinked material, comprising reacting a mixture comprising (a) a silyl-hydride containing polymer, (b) a mono-unsaturated olefin or an unsaturated polyolefin, or combinations thereof and (c) a catalyst, optionally in the presence of a solvent, in order to produce the crosslinked material, wherein the catalyst is a complex of the Formula (I) or an adduct thereof

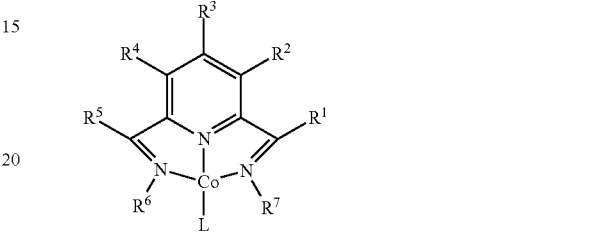

wherein
each occurrence of $R^1$, $R^2$, $R^3$, $R^4$, and $R^5$ is independently hydrogen, C1-C18 alkyl, a C1-C18 substituted alkyl, an aryl, a substituted aryl, or an inert substituent, wherein one or more of $R^1$-$R^5$, other than hydrogen, optionally contain at least one heteroatom; each occurrence of $R^6$ and $R^7$ is independently C1-C18 alkyl, C1-C18 substituted alkyl, aryl or substituted aryl, wherein $R^6$ and $R^7$ optionally contain at least one heteroatom; optionally any two of $R^1$-$R^7$ vicinal to one another, $R^1$-$R^2$, and/or $R^4$-$R^5$ taken together may form a ring being a substituted or unsubstituted, saturated or unsaturated cyclic structure, with the proviso that $R^1$-$R^7$ and $R^8$-$R^6$ are not taken to form a terpyridine ring; and
L is hydroxyl, or a C1-C18 alkyl, C1-C18 substituted alkyl, aryl, or substituted aryl group, wherein L optionally contains at least one heteroatom.

36. The process of claim 35, wherein the reaction is conducted under an inert atmosphere.

37. The process of claim 35, wherein the reaction is conducted in the presence of a solvent selected from the group consisting of hydrocarbons, halogenated hydrocarbons, ethers, and combinations thereof.

38. The process of claim 35, wherein the reaction is carried out at a temperature of −40° C. to 200° C.

39. The process of claim 1, wherein the catalyst is present in an amount of from about 0.1 mol % to about 5 mol %.

40. The process of claim 5, wherein the catalyst is present in an amount of from about 0.1 mol % to about 5 mol %.

* * * * *